(12) United States Patent
Kshirsagar et al.

(10) Patent No.: US 10,427,131 B2
(45) Date of Patent: *Oct. 1, 2019

(54) GUANIDINE-FUNCTIONALIZED PERLITE PARTICLES, ARTICLES CONTAINING THE PARTICLES, AND METHODS OF USING THE PARTICLES AND ARTICLES

(71) Applicant: 3M INNOVATIVE PROPERTIES COMPANY, St. Paul, MN (US)

(72) Inventors: Manjiri T. Kshirsagar, Woodbury, MN (US); George W. Griesgraber, Eagan, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 30 days.

This patent is subject to a terminal disclaimer.

(21) Appl. No.: 15/555,679

(22) PCT Filed: Mar. 15, 2016

(86) PCT No.: PCT/US2016/022409
§ 371 (c)(1),
(2) Date: Sep. 5, 2017

(87) PCT Pub. No.: WO2016/149233
PCT Pub. Date: Sep. 22, 2016

(65) Prior Publication Data
US 2018/0038862 A1    Feb. 8, 2018

Related U.S. Application Data

(60) Provisional application No. 62/135,303, filed on Mar. 19, 2015.

(51) Int. Cl.
| B01J 20/10 | (2006.01) |
| B01J 20/22 | (2006.01) |
| B01J 20/28 | (2006.01) |
| B01J 20/32 | (2006.01) |
| G01N 33/543 | (2006.01) |
| G01N 33/552 | (2006.01) |
| G01N 33/569 | (2006.01) |

(52) U.S. Cl.
CPC ............ *B01J 20/106* (2013.01); *B01J 20/22* (2013.01); *B01J 20/28026* (2013.01); *B01J 20/28035* (2013.01); *B01J 20/3204* (2013.01); *B01J 20/3259* (2013.01); *G01N 33/54313* (2013.01); *G01N 33/54353* (2013.01); *G01N 33/552* (2013.01); *G01N 33/569* (2013.01); *G01N 33/56916* (2013.01); *G01N 33/56938* (2013.01)

(58) Field of Classification Search
CPC .. B01J 20/106; B01J 20/3259; B01J 20/3204; B01J 20/28035; B01J 20/22; B01J 20/28026; G01N 33/56938; G01N 33/552; G01N 33/56916; G01N 33/54353; G01N 33/569; G01N 33/54313
See application file for complete search history.

(56) References Cited

U.S. PATENT DOCUMENTS

| 4,118,531 A | 10/1978 | Hauser |
| 4,772,488 A | 9/1988 | Pinch |
| 5,238,812 A | 8/1993 | Coulter |
| 5,369,011 A | 11/1994 | Ebersole |
| 5,576,185 A | 11/1996 | Coulter |
| 5,597,645 A | 1/1997 | Pike |
| 7,374,684 B2 | 5/2008 | Gibson |
| 7,422,868 B2 | 9/2008 | Fan |
| 9,657,038 B2 | 5/2017 | Griesgraber |
| 2010/0190171 A1 | 7/2010 | Kshirsagar |
| 2010/0273143 A1 | 10/2010 | Brewer |
| 2010/0326902 A1 | 12/2010 | Midkiff |
| 2011/0217752 A1* | 9/2011 | Rasmussen ............ C08G 69/10 435/183 |

(Continued)

FOREIGN PATENT DOCUMENTS

| CA | 2612854 | 6/2008 |
| WO | 1989-09279 | 10/1989 |

(Continued)

OTHER PUBLICATIONS

'1-Propanarnine,3-(triethoxysilyI)-.' NIST Chemistry WebBook. [online]. [retrieved on Mar. 31, 2019]. 2018. Retrieved from the Internet <URL: https://webbook.nist.gov/cgi/cbook.cgi?ID=919-30-2>. (Year: 2018).*

'N-(2-Arninoethyl)-3-aminopropyltrimethoxysilane'. NIST Chemistry WebBook. [online]. [retrieved on Mar. 31, 2019]. 2018. Retrieved from the Internet < https://webbook.nist.gov/cgi/cbook.cgi?ID=1760-24-3>. (Year: 2018).*

International Search report for PCT International Application No. PCT/US2016/022409 dated Jun. 26, 2016, 5 pages.

*Primary Examiner* — Renee Claytor
*Assistant Examiner* — Susan E. Fernandez
(74) *Attorney, Agent, or Firm* — Adrian L. Pishko

(57) ABSTRACT

Guanidine-functionalized perlite particles are provided. Nonwoven articles are also provided, including a fibrous porous matrix and guanidine-functionalized perlite particles enmeshed in the fibrous porous matrix. Laminated articles are additionally provided, including a first substrate and a second substrate sealed to the first substrate along at least a portion of a perimeter of the first substrate. The laminated article further includes guanidine-functionalized perlite particles disposed between the first substrate and the second substrate. Methods of detecting microorganisms or target cellular analytes in a fluid sample using guanidine-functionalized particles or laminated articles are also provided.

18 Claims, 1 Drawing Sheet

(56) References Cited

U.S. PATENT DOCUMENTS

2013/0244225 A1 9/2013 Kshirsagar
2013/0260370 A1 10/2013 Kshirsagar
2016/0289249 A1* 10/2016 Kshirsagar ............. B01D 39/14

FOREIGN PATENT DOCUMENTS

| WO | 2010-078404 | 7/2010 |
|----|-------------|--------|
| WO | 2011-109151 | 9/2011 |
| WO | 2014-088807 | 6/2014 |
| WO | 2015-047464 | 4/2015 |
| WO | 2015-094938 | 6/2015 |
| WO | 2016-149235 | 9/2016 |
| WO | 2016-149472 | 9/2016 |

* cited by examiner

GUANIDINE-FUNCTIONALIZED PERLITE PARTICLES, ARTICLES CONTAINING THE PARTICLES, AND METHODS OF USING THE PARTICLES AND ARTICLES

CROSS REFERENCE TO RELATED APPLICATIONS

This application is a national stage filing under 35 U.S.C. 371 of PCT/US2016/022409, filed Mar. 15, 2016, which claims the benefit of U.S. Application No. 62/135,303, filed Mar. 19, 2015, the disclosure of which is incorporated by reference in its/their entirety herein.

FIELD

The present disclosure relates to guanidine-functionalized perlite particles, nonwoven articles, laminated articles, and methods of using the particles, nonwoven articles, and laminated articles, such as for detecting microorganisms in a fluid sample.

BACKGROUND

It is often desirable or necessary to assay for the presence of bacteria or other microorganisms in various clinical, food, environmental, or other samples, in order to determine the identity and/or the quantity of the microorganisms present. Bacterial DNA or bacterial RNA, for example, can be assayed to assess the presence or absence of a particular bacterial species even in the presence of other bacterial species. The ability to detect the presence of a particular bacterium, however, depends, at least in part, on the concentration of the bacterium in the sample being analyzed. Concentration of the bacteria in the sample can shorten the culturing time or even eliminate the need for a culturing step. Thus, methods have been developed to isolate (and thereby concentrate) particular bacterial strains by using antibodies specific to the strain (for example, in the form of antibody-coated magnetic or non-magnetic particles). Such methods, however, have tended to be expensive and still somewhat slower than desired for at least some diagnostic applications. Non-specific concentration or capture of microorganisms has been achieved through methods based upon carbohydrate and lectin protein interactions. Various inorganic materials (for example, hydroxyapatite and metal hydroxides) have also been used to non-specifically bind and concentrate bacteria. Such non-specific concentration methods have varied in speed, cost, sample requirements, space requirements, ease of use, suitability for on-site use, and/or effectiveness.

Rapid methods based on ATP bioluminescence assays have been used to determine microbial contamination in water as they provide immediate results; however, the methods are limited by detection sensitivity because they require at least $1 \times 10^5$ colony forming units (cfu)/ml to elicit detectable responses. One can increase the sensitivity of the ATP bioluminescence assay by using a larger volume of sample (e.g., 100 ml), but such methods can be difficult to implement in the field.

SUMMARY

Guanidine-functionalized perlite particles are provided, as well as nonwoven articles and laminated articles containing the particles, which can be used to detect microorganisms and/or cellular analytes in fluid samples.

In a first aspect, a guanidine-functionalized perlite particle is provided. The guanidine-functionalized perlite particle includes a perlite particle that is modified with at least one silane having the formula $X_{3-n}R^a{}_n Si\text{—}Y\text{-}G$. In the formula, n is 0, 1, or 2 and each $R^a$, if present, is independently an alkyl, aralkyl, or aryl. In the formula, Y is a divalent group comprising an alkylene having 2 to 20 carbons, G is a guanidine group of the formula —NH—C(=NH)—NH$_2$, and each X is independently alkoxy or acyloxy.

In a second aspect, a nonwoven article is provided. The nonwoven article includes a fibrous porous matrix and a plurality of guanidine-functionalized perlite particles enmeshed in the fibrous porous matrix.

In a third aspect, a laminated article is provided. The laminated article includes a first substrate and a second substrate sealed to the first substrate along at least a portion of a perimeter of the first substrate. The laminated article further includes a plurality of guanidine-functionalized perlite particles disposed between the first substrate and the second substrate.

In a fourth aspect, a method of detecting microorganisms or target cellular analytes in a fluid sample is provided. The method includes providing a laminated article according to the third aspect and providing a fluid sample suspected of containing at least one microorganism strain or target cellular analyte. The method further includes contacting the fluid sample with the laminated article such that at least a portion of the at least one microorganism strain or target cellular analyte is bound to the laminated article and detecting the presence of the at least one bound microorganism strain or bound target cellular analyte.

In a fifth aspect, another method of detecting microorganisms or target cellular analytes in a fluid sample is provided. The method includes providing a plurality of guanidine-functionalized perlite particles according to the second aspect and providing a fluid sample suspected of containing at least one microorganism strain or target cellular analyte. The method further includes contacting the fluid sample with the plurality of guanidine-functionalized perlite particles such that at least a portion of the at least one microorganism strain or target cellular analyte is bound to the guanidine-functionalized perlite particles and detecting the presence of the at least one bound microorganism strain or bound target cellular analyte.

DETAILED DESCRIPTION

Figure 1:
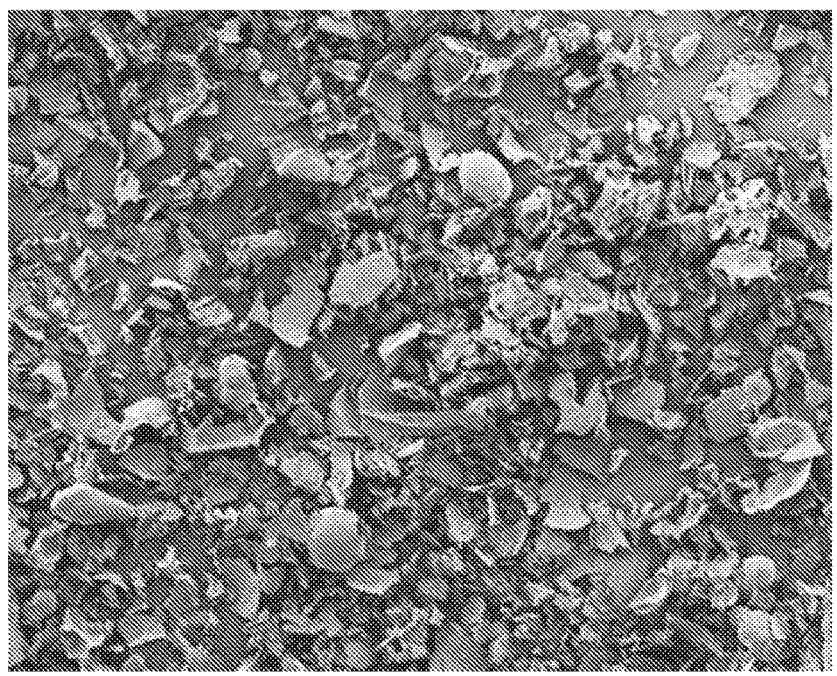
FIG. 1 is a scanning electron microscope (SEM) image of the exemplary guanidine-functionalized perlite particles of Example 1.
Figure 2:
FIG. 2 is an SEM image of the exemplary nonwoven article of Example 3.

Guanidine-functionalized perlite particles, nonwoven articles and laminated articles including the particles, and rapid methods for monitoring of microbial content of fluid samples are provided. The guanidine-functionalized particles concentrate at least one microorganism or target cellular analyte and allow detection of the bound microorganism or target cellular analyte. The guanidine-functionalized particles, nonwoven articles, and laminated articles may be contacted with large volumes of fluid samples to concentrate the microorganism and/or target cellular analyte, and also allow further optional washing to remove contaminants prior to detection. Methods according to the disclosure are capable of readily detecting bacterial contamination in fluid samples in about 15 minutes. Accordingly, the guanidine-functionalized particles, nonwoven articles, laminated articles, and methods can be suitable for field based detection of microorganisms and target cellular analytes in fluid samples.

For the following Glossary of defined terms, these definitions shall be applied for the entire application, unless a different definition is provided in the claims or elsewhere in the specification.

Glossary

Certain terms are used throughout the description and the claims that, while for the most part are well known, may require some explanation. It should be understood that, as used herein:

The term "a", "an", and "the" are used interchangeably with "at least one" to mean one or more of the elements being described. The term "and/or" means either or both. For example "A and/or B" means only A, only B, or both A and B.

As used in this specification, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

The term "comprises" and variations thereof do not have a limiting meaning where these terms appear in the description and claims.

The term "consists essentially of" does not exclude the presence of additional materials which do not significantly affect the desired characteristics of a given composition or product.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

The term "acyloxy" refers to a monovalent group of formula —O(CO)R where R is an alkyl group.

The term "alkoxy" refers to a monovalent group of formula —OR where R is an alkyl group.

The term "alkyl" refers to a monovalent group that is a radical of an alkane and includes groups that are linear, branched, cyclic, or combination thereof. The alkyl group typically has 1 to 30 carbon atoms. In some embodiments, the alkyl group contains 1 to 20 carbon atoms, 1 to 10 carbon atoms, 1 to 6 carbon atoms, or 1 to 4 carbon atoms. Examples of alkyl groups include, but are not limited to, methyl, ethyl, n-propyl, isopropyl, n-butyl, isobutyl, tert-butyl, n-pentyl, n-hexyl, cyclohexyl, n-heptyl, n-octyl, and ethylhexyl.

The term "alkylene" refers to a divalent group that is a radical of an alkane. The alkylene can be straight-chained, branched, cyclic, or combination thereof. The alkylene typically has 1 to 200 carbon atoms. In some embodiments, the alkylene contains 1 to 100, 1 to 80, 1 to 50, 1 to 30, 1 to 20, 1 to 10, or 1 to 4 carbon atoms. The radical centers of the alkylene can be on the same carbon atom (i.e., an alkylidene) or on different carbon atoms.

The term "aralkyl" refers to a monovalent group that is a radical of the compound R—Ar where Ar is an aromatic carbocyclic group and R is an alkyl group.

The term "aryl" refers to a monovalent group that is a radical of a carbocyclic aromatic compound. The aryl can have one aromatic ring or can include up to 5 other carbocyclic rings that are connected to or fused to the aromatic ring. The other carbocyclic rings can be aromatic, non-aromatic, or combination thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

The term "cellular analyte" means an analyte of cellular origin (that is, a microorganism or a component thereof (for example, a cell or a cellular component such as deoxyribonucleic acid (DNA) or ribonucleic acid (RNA), proteins, nucleotides such as adenosine triphosphate (ATP), and the like, and combinations thereof); references to a microorganism or microorganism strain throughout this specification are meant to apply more generally to any cellular analyte).

The term "concentration agent" means a material or composition that binds microorganisms and/or cellular analytes from a fluid sample (preferably, having a cellular analyte capture or binding efficiency of at least about 60 percent, or at least about 70 percent, or at least about 80 percent, or at least about 90 percent), thereby concentrating the microorganisms and/or cellular analytes into a smaller volume than when present in the fluid sample. The concentration agent according to this disclosure comprises guanidine-functionalized perlite particles.

The term "detection" means the identification of a microorganism or of a cellular analyte (for example, at least a component of a target microorganism, which thereby determines that the target microorganism is present).

The term "enmeshed" (in regard to particles in a fibrous porous matrix) means that the particles are entrapped in and on the fibrous porous matrix (and, preferably, distributed within it), rather than solely being borne on its surface.

The term "fibrillated" (in regard to fibers or fibrous material) means treated (for example, by beating) in a manner that forms fibrils or branches attached to a fiber's main trunk.

The term "fibrous porous matrix" means a nonwoven web or medium, (i.e., not a woven or knitted fabric), comprising interlaid fibers, for example, a web comprising fibers that are interlaid by meltblowing, spunbonding, or other air laying techniques; carding; wet laying; or the like. Typically, the fibers have lengths of less than 100 millimeters and are uncrimped.

The term "filtering" is generally used to describe the process of separating matter by size, charge and/or function. For example, filtering can include separating soluble matter and a solvent (e.g., diluent) from insoluble matter, or it can include separating soluble matter, a solvent and relatively small insoluble matter from relatively large insoluble matter. A variety of filtration methods can be used, including, but not limited to, passing the liquid composition through a filter, settling followed by aspiration or decanting, other suitable filtration methods, and combinations thereof "Settling" is used to refer to allowing the insoluble matter in the liquid composition to settle. Settling may occur by gravity or by centrifugation. The insoluble matter (or relatively large insoluble matter) can then be separated from the soluble matter (or soluble matter and relatively small insoluble matter) and solvent by aspirating the soluble matter and solvent from the insoluble matter, decanting the soluble matter and solvent, or a combination thereof.

The term "filtrate" is generally used to describe the liquid remaining after the insoluble matter (or at least the relatively large insoluble matter) has been removed from the liquid composition.

The term "fluid" means liquid, solution, or dispersion of solid or liquid in liquid.

The term "laminated" means an article having a plurality of stacked layers (for example, an article having a first substrate layer, a particle layer disposed on the first substrate layer, and a second substrate layer disposed on the particle layer).

The term "microorganism" means any cell or particle having genetic material suitable for analysis or detection (including, for example, bacteria, yeasts, viruses, and bacterial endospores).

The term "microorganism strain" means a particular type of microorganism that is distinguishable through a detection method (for example, microorganisms of different genera, of different species within a genera, or of different isolates within a species).

The term "polygon" means a shape having three or more sides.

The terms "polymer" and "polymeric material" are used interchangeably and refer to materials formed by reacting one or more monomers.

The term "sample" means a substance or material that is collected (for example, to be analyzed).

The term "sample matrix" means the components of a sample other than microorganisms and/or cellular analytes.

The term "target cellular analyte" means any cellular analyte that is desired to be detected.

The term "target microorganism" means any microorganism that is desired to be detected.

The term "through pore" (in reference to a porous matrix) means a pore that comprises a passageway or channel (with separate inlet and outlet) through the porous matrix.

Reference throughout this specification to "one embodiment," "certain embodiments," "one or more embodiments" or "an embodiment," whether or not including the term "exemplary" preceding the term "embodiment," means that a particular feature, structure, material, or characteristic described in connection with the embodiment is included in at least one embodiment of the certain exemplary embodiments of the present disclosure. Thus, the appearances of the phrases such as "in one or more embodiments," "in some embodiments," "in certain embodiments," "in one embodiment," "in many embodiments" or "in an embodiment" in various places throughout this specification are not necessarily referring to the same embodiment of the certain exemplary embodiments of the present disclosure. Furthermore, the particular features, structures, materials, or characteristics may be combined in any suitable manner in one or more embodiments.

Various exemplary embodiments of the disclosure will now be described. Exemplary embodiments of the present disclosure may take on various modifications and alterations without departing from the spirit and scope of the disclosure. Accordingly, it is to be understood that the embodiments of the present disclosure are not to be limited to the following described exemplary embodiments, but are to be controlled by the limitations set forth in the claims and any equivalents thereof.

In a first aspect, a guanidine-functionalized perlite particle is provided. The guanidine-functionalized perlite particle includes a perlite particle that is modified with at least one guanidine-containing ligand. Perlite is a naturally-forming amorphous volcanic glass, containing about 70-75% silicon dioxide and 12-15% aluminum oxide, as well as smaller amounts of other metal oxides, including sodium oxide, potassium oxide, iron oxide, magnesium oxide, and calcium oxide. When perlite is expanded by heat it forms a lightweight aggregate, to about four to twenty times its initial volume. Perlite has been used in applications such as construction applications (e.g., as an insulator or texturizer), horticultural applications (e.g., to provide aeration and moisture retention or as a carrier for fertilizer or other active agents), and industrial applications (e.g., as an abrasive, filler, or filter media for water and other fluid samples). Examples of suitable perlite particles include the 4106 grade material, 4156 grade material, and the 476 grade material, both commercially available from Dicaperl Minerals Corporation (Crawfordsville, Ind.).

The guanidine-containing ligand is formed by modifying the perlite particle with a guanidine-containing silane having the structure shown in Formula 1:

$$X_{3-n}R^a_nSi-Y-G \qquad \text{Formula 1}$$

In Formula 1, Si is a silicon atom, and G denotes a guanidine group of the formula $-NH-C(=NH)-NH_2$. Y is a divalent group that is covalently bonded to the silicon atom at one end and to the G group at the other end. Each $R^a$ group, if any are present, is independently an alkyl, aralkyl, or aryl group, and is attached to the silicon atom. Each X is a leaving group covalently bonded to the silicon atom and is independently alkoxy or acyloxy, and n is 0, 1, or 2.

A typical alkylene can be up to 20, up to 16, 12, 10, 8, 7, 6, 5, 4, or even up to 3 carbons, or even 2 carbons, inclusive of the terminal atoms of the divalent group. In some embodiments, Y is a divalent group comprising an alkylene of 3 to 6 carbons. In a preferred embodiment, Y is a divalent group having 3 carbons (i.e., propyl).

In Formula 1, each leaving group X is independently an alkoxy group of 1, 2, 3, 4, 5, 6, 7, 8, 9, or even up to 10 carbons, or is an acyloxy group of 2 carbons, or 3, 4, 5, 6, 7, 8, 9, or even up to 10 carbons, where the alkoxy or acyloxy group is bonded to the silicon through an oxygen atom.

In some embodiments, n is 0. When n is 0, no $R^a$ groups are present, and Formula 1 can be re-written more simply as shown in Formula 2 (where Si, G, Y, and X are as defined for Formula 1):

$$X_3Si-Y-G \qquad \text{Formula 2}$$

When the silane of Formula 1 (or Formula 2) reacts with an $-OH$ group on the surface of a perlite particle, at least one X leaving group is replaced by a covalent bond of between the silicon atom and an oxygen atom on the surface of the perlite particle. An embodiment of a guanidine-functionalized perlite particle comprising a specific exemplary guanidine-containing ligand within the general type represented by Formula 1, wherein n=0 (i.e., as in Formula 2), is shown in Formula 3 (the circle in Formula 3 represents a perlite particle):

Formula 3

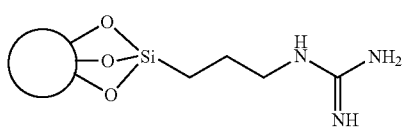

It will be understood that Formula 3 represents a specific embodiment wherein n is 3 and Y is a divalent group that is alkylene having 3 carbons. In each of Formulas 1 to 3, the ionization state of the guanidine group is omitted; however, it will be understood that in various environments such guanidine groups may be charged or uncharged (e.g., protonated or deprotonated), for example, according to the pH of a liquid medium in which the guanidine group is present, as discussed later herein.

The covalent bond(s) between the oxygen(s) of the ligand and the particle can be conveniently obtained, for example, by reacting a Si-bonded hydrolyzable group of the guanidine-containing precursor with a hydroxyl group of the particle, as discussed in detail later herein. While the exemplary structure of Formula 3 shows three such bonded oxygen atoms (i.e., n=3 in Formula 1), it will be appreciated that in various embodiments one, two or three such bonded oxygen atoms can be provided. If less than three such oxygen atoms are bonded to the silicon atom, other substituents (e.g., substituents that are not bonded to the particle, and which are not shown in Formula 1) may be present on the silicon atom. For example, the guanidine-containing ligand can include a polymeric structure involving formation of Si—O—Si (i.e., siloxane) groups, resulting from Si—O bonds being formed between two or more guanidine-containing ligand precursors. Without being bound by theory, it is thought that Si—O—Si groups may form in the presence of added water, or other aqueous solvents, or other agent that can hydrolyze bonds in Si—O—R groups, to give rise to more complex guanidine-containing ligand structures attached to particles, including such possible structures as shown in the non-limiting examples of Formulas 4a to 4d (each R in Formulas 4a to 4d independently being H or lower alkyl (e.g., methyl), or even another Si atom in which may or may not be attached to the perlite particle through an Si—O— bond; the circle in each of Formulas 4a to 4d represents a perlite particle):

Formula 4a

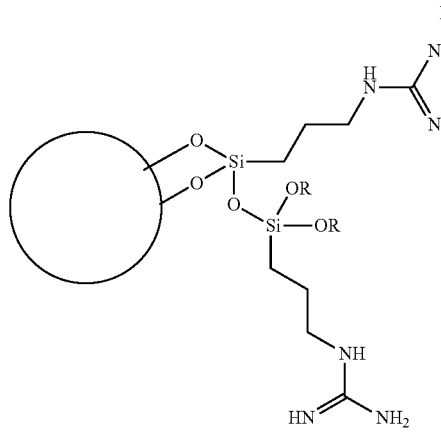

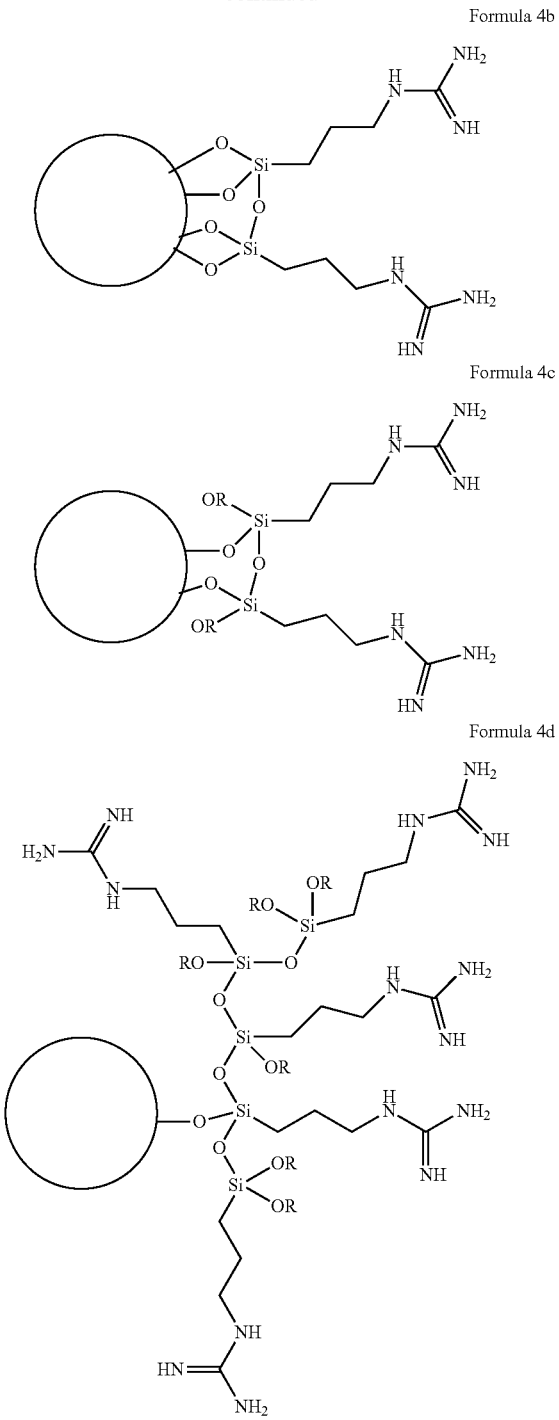

It is seen from Formulas 4a to 4d that a network of polymerized guanidine-containing ligands can form a coating on the surface of the perlite particle. In some embodiments it may be desirable to obtain the particle functionalized with polymerized guanidine-containing ligand (e.g., as in any of the non-limiting polymerized guanidine-containing ligand structures shown in Formulas 4a to 4d, or the like, having at least one Si—O—Si group in the polymerized guanidine-containing ligand), as a means of increasing the loading of nitrogen-containing guanidine groups on the surface of the perlite particle. It is thought that in at least these types of polymerizations, a loading of nitrogen-containing guanidine groups on the surface of the perlite particle can attain levels of surface nitrogen content in a range from 1 to 10 atomic percent, as can be measured, for example, by X-ray photoelectron spectroscopy.

Concentration agent particles are water-insoluble particulate materials that have been employed to non-specifically capture microorganism strains, cellular analytes, or a combination thereof, when contacted with fluid samples containing microorganisms and/or cellular analytes. The concentration agent particles typically comprise microparticles.

The guanidine-functionalized perlite particles used in nonwoven articles of the present disclosure can be used in essentially any particulate form (preferably, a relatively dry or volatiles-free form) that is amenable to blending with fibers to form the nonwoven articles of the present disclosure, or amenable to encapsulating between two substrates to form the laminated articles of the present disclosure. Preferably, the guanidine-functionalized perlite particles are used in the form of a powder. Useful powders include those that comprise microparticles (preferably, microparticles having a particle size in the range of about 1 micrometer (more preferably, about 2 micrometers; even more preferably, about 3 micrometers; most preferably, about 4 micrometers) to about 100 micrometers (more preferably, about 50 micrometers; even more preferably, about 25 micrometers; most preferably, about 15 or 20 micrometers; where any lower limit can be paired with any upper limit of the range, as referenced above).

X-ray photoelectron spectroscopy ("XPS", also known as Electron Spectroscopy for Chemical Analysis ("ESCA")) is a technique that can provide information about the elemental and chemical (oxidation state and/or functional group) concentrations present on a solid surface. XPS typically provides an analysis of the outermost 3 to 10 nanometers (nm) of the specimen surface. XPS is sensitive to all elements in the periodic table except hydrogen and helium with detection limits for most species in the 0.1 to 1 atomic percent concentration range. In some cases, for example for perlite particles, a preferred surface composition assessment conditions for XPS can include a take-off angle of 45 degrees measured with respect to the sample surface with a solid angle of acceptance of ±20 degrees. A person skilled in the art can select a suitable instrument setting for analysis of particles of the present disclosure. Suitable guanidine-functionalized perlite particles for use according to the present disclosure include those that comprise perlite and that have a surface composition having a surface nitrogen content of greater than 2 and less than or equal to about 12, as determined by XPS.

It will be appreciated that a guanidine group as described herein may be uncharged or charged (e.g., protonated) depending on the particular environment in which it is placed (e.g., depending on the pH of an aqueous buffer with which the guanidine-functionalized particle is brought into contact). In environments in which a guanidine group of a guanidine-functionalized particle is charged, the charged guanidine group may comprise an associated counterion. In some embodiments such a counterion may arise in the generation of the guanidine group (that is, the guanidine group as produced in the synthesis reaction may be charged, and may have a counterion associated therewith, as discussed later herein). In other embodiments a counterion may not arise in the generation of the guanidine group (e.g., the guanidine group may be produced in the synthesis reaction as a free base), but the guanidine-containing ligand (e.g., the functionalized particle) may be later placed into an environment (e.g., a liquid buffer) in which the guanidine group becomes charged and a corresponding counterion becomes associated therewith. In still other embodiments, a particular counterion may be associated with the guanidine group (e.g. as synthesized), but the counterion may then be exchanged for a different counterion. The charge state of a guanidine group and the presence and identity and charge state of a counterion thus possibly varying with environment, it is emphasized that all references to guanidine groups in the claims herein, are irrespective of the charge state of the guanidine group and are irrespective of the presence or identity of an associated counterion, unless such charge state and/or presence and/or identity of a counterion is explicitly specified in the claim.

Furthermore, the concept of a counterion that is associated with a guanidine group is used broadly herein, and it will be understood that such a counterion may not necessarily be constantly located in close proximity to the same guanidine group. Furthermore, the guanidine group and the associated counterion do not necessarily have to always be fully solvated (e.g., in aqueous solution). That is, they may be present as salts in a partially or substantially dried product (e.g., a solid or semi-solid product), which product may be placed into a liquid (e.g., an aqueous buffer) and solvated as desired. In specific embodiments, the associated counterion is a sulfate and/or bisulfate ion. In other specific embodiments, the associated counterion is a hydroxide ion (as may result, for example, from putting a guanidine group in the free-base form into an unbuffered aqueous solution).

In some embodiments, a guanidine-functionalized particle can be made by a simple and convenient method using an O-alkylisourea, or a salt thereof (for example, O-methylisourea hemisulfate, which is a readily available starting material, CAS No. 52328-05-9). In a first step of this method, an O-alkylisourea may be reacted with a linker molecule of the general structure shown in Formula 5:

                                                                                                                     Formula 5

In Formula 5, Si is a silicon atom, and $NH_2$ denotes a primary amino group. Y is a divalent group that is covalently bonded to the silicon atom at one end and to the primary amino group at the other end. Each $R^a$ group, if any are present, is independently an alkyl, aralkyl, or aryl group, and is attached to the silicon atom (noting that no $R^a$ group will be present when n is 0). Each X is a leaving group covalently bonded to the silicon atom and is independently alkoxy or acyloxy, and n is 0, 1, or 2.

In some embodiments, Y is a divalent alkylene group. A typical alkylene can be up to 20, up to 16, 12, 10, 8, 7, 6, 5, 4, or even up to 3 carbons, or even 2 carbons. In some embodiments, Y is a divalent group comprising an alkylene of 3 to 6 carbons. In a preferred embodiment, Y is a divalent group having 3 carbons (i.e., propyl), as shown, for example in the preferred linker compound of Formula 6.

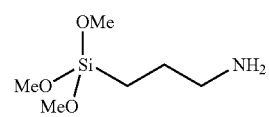
                                                                                                                     Formula 6

In some embodiments, a first step of a method of making a guanidine-functionalized perlite particle is shown in Reaction Scheme 1, reacting a compound of Formula 5 with an O-alkylisourea (R' can be methyl or other lower alkyl, including anywhere from 2 to 10 carbons). The reaction can be carried out in a suitable solvent (e.g., methanol or ethanol).

Reaction Scheme I

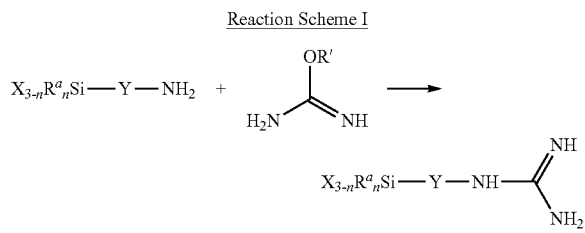

In a more specific embodiment of Reaction Scheme I, the compound of Formula 6 is reacted with an O-methylisourea salt, as shown in Reaction Scheme II.

Reaction Scheme II

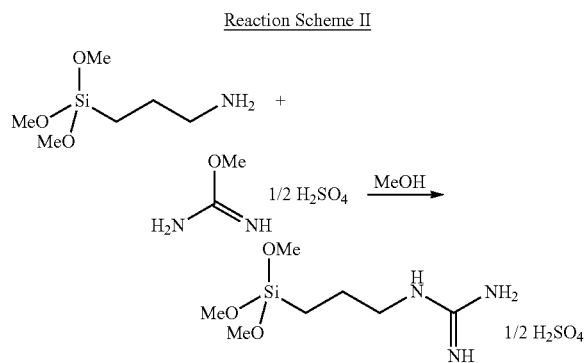

In Reaction Scheme II, O-methylisourea is provided as a hemisulfate, and is reacted with 3-aminopropyltrimethoxysilane (in methanol) to form the guanidine group (noting that the charge state of the guanidine group and of the associated hemisulfate counterion are not shown in Reaction Scheme II).

It will be appreciated that Formula 6 and Reaction Scheme II are representative examples and that any suitable linker molecule can be used (as long as the linker molecule includes, e.g., a primary amine that can be reacted with the O-methylisourea to form a guanidine group), within the overall boundaries prescribed herein. For example, the linker molecule can comprise any desired number of any suitable reactive groups (e.g., ethoxy, methoxy, acetoxy) on the silicon atom (noting that if multiple reactive groups are present they do not have to be identical; further noting that if less than three such reactive groups are used, other (e.g., $R^a$) groups can be present, e.g. as shown in the general representation of Formula 4, and still further noting that if multiple $R^a$ groups are present they do not have to be identical). In a specific example, 3-aminopropyltriethoxysilane may be used as the linker molecule rather than the 3-aminopropyltrimethoxysilane of Formula 6 and included in Reaction Scheme II.

In some embodiments, Y is a divalent group comprising an alkylene, and the divalent group can further optionally comprise other groups, including an arylene, oxy, —NH—, or a combination thereof. In some specific embodiments, the divalent Y group of the linker molecule may comprise a secondary amine. In a particular example of this type, the linker molecule may be e.g. N-(2-aminoethyl)-3-aminopropyltrimethoxysilane (available under the trade designation "SIA0591.0" from Gelest, Inc., Tullytown, Pa.). Other potentially useful linker molecules may include e.g. (aminoethylaminomethyl) phenethyltrimethoxysilane ("SIA0588.0", Gelest), N-(2-aminoethyl)-3-aminopropylmethyldimethoxysilane ("SIA0589.0", Gelest), N-(6-aminohexyl) aminopropyltrimethoxysilane ("SIA0594.0", Gelest), N-(2-aminoethyl)-11-aminoundecyl-trimethoxysilane ("SIA0595.0", Gelest), N-3[(amino(polypropylenoxy)] aminopropyltrimethoxysilane ("SIA0599.4", Gelest), 3-aminopropylmethyldiethoxysilane ("SIA0605.0", Gelest), 3-aminopropyltriethoxysilane ("SIA0610.0", Gelest), and (3-trimethoxysilylpropyl)diethylene-triamine ("SIT8398.0", Gelest). Mixtures of any of the herein-mentioned linker molecules may be used if desired.

In a second step of this method, at least one of the Si-bonded X groups of the linker molecule (with Si atoms comprising one or more such reactive alkoxy or acyloxy groups being well known by the term silane coupling agents) is reacted with a hydroxyl group of a suitable particle to form a covalent bond between the linker molecule and the particle. (It is emphasized that the terminology of "first" and "second" steps is used purely for convenience of description and that the steps can be performed in any desired order). For example, any or all of the three trimethoxy reactive groups of the linker molecule in Reaction Scheme II may react with surface hydroxyl groups of the particle. In some embodiments, and as mentioned above, the addition of water in the second step of this method has been observed to result in higher surface nitrogen values as measured by XPS (see Example section). The amount of water added can be in a range from 0 to 5 equivalents ("eq") of water relative to the amount of linker molecule ("equivalents" here refers to "molar equivalents", defined as 1 mole of water for each 1 mole of linker molecule), which can include up to 1 eq, or up to 2 eq, up to 1 eq, up to 0.5 eq, up to 0.25 eq, or even any value in between 0 eq and 5 eq of water, relative the amount of linker molecule.

In one embodiment, the net result of these two steps is summarized in exemplary embodiment in Formula 7 (the circle in Formula 7 represents a perlite particle):

Formula 7

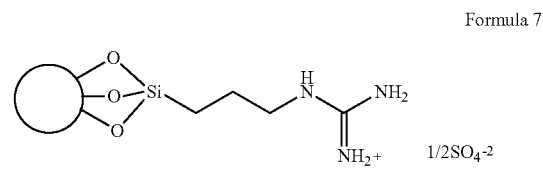

The specific exemplary representation of Formula 7 shows the thus-produced guanidine group in a positively charged (e.g., protonated) condition with a negatively charged hemisulfate counterion associated therewith. It will be understood that a guanidine-functionalized particle may be produced in such condition by the above method, but that the charge state of the guanidine group, the presence, identity and/or charge state of a counterion, etc., may be affected thereafter by the environment into which the guanidine-functionalized particle is placed, as discussed above.

The general methods-of-making described above, and materials used therein, may be tailored as desired for particular purposes. Thus, in some embodiments, each thus-formed guanidine-containing ligand on the particle may only have a single guanidine group (rather than there being e.g. two, three or more guanidine groups on a given guanidine-containing ligand). In some embodiments, the thus-formed guanidine-comprising ligands may be the only ligands on the particle (rather than there being additional ligands, e.g. silane-coupled ligands, on the particle, which additional ligands do not comprise a guanidine group). In some embodiments, a substantial amount (e.g., an amount readily detectable by surface analysis) of residual hydroxyls are present on the surface of the particle even after the attachment of the linker molecules to some of the hydroxyls of the particle to form ligands thereon (e.g., rather than the residual hydroxyls being endcapped). In some embodiments, the methods disclosed herein do not include a step of equilibrating the particle in an atmosphere having a defined relatively humidity (e.g., of less than 40%) prior to the reacting of the linker molecule with a surface hydroxyl group of the particle. While the method outlined in Reaction Scheme II uses an O-methylisourea, it will be appreciated that other starting materials might be used to make a guanidine-functionalized linker of the general structure of Formula 1. Such starting materials might include e.g. O-alkylisourea salts such as O-methylisourea sulfate, O-methylisourea hydrogen sulfate, O-methylisourea acetate, O-ethylisourea hydrogen sulfate, and O-ethylisourea hydrochloride. Beyond these materials, other starting materials that might be used to make a guanidine-functionalized linker of the general structure of Formula 1 might include e.g. cyanamide, chloroformamidine hydrochloride; 1-amidino-1,2,4-triazole hydrochloride; 3,5-dimethylpyrazole-1-carboxamidine nitrate; pyrazole-1-carboxamidine hydrochloride; N-amidinopyrazole-1-carboxamidine hydrochloride. It will be appreciated that some of these starting materials may produce a guanidine-containing linker in which the guanidine group is in a specific charge state (e.g., is a free base or is positively charged) and/or has a specific counterion associated therewith. It will be understood that such a guanidine group may be placed into a specific charge state, may have its associated counterion exchanged for some other counterion, and so on, based on the disclosures herein.

In a second aspect, a nonwoven article is provided. The nonwoven article includes a fibrous porous matrix and a plurality of guanidine-functionalized perlite particles enmeshed in the fibrous porous matrix. The nonwoven fibrous porous matrix is often in the form of a layer of interlaid fibers that are not woven or knitted together. The nonwoven, fibrous porous matrix can be prepared by any suitable process such as, for example, air laying techniques, spunlaid techniques such as meltblowing or spunbonding, carding, wetlaying, and combinations thereof. In many embodiments, the fibrous nonwoven matrix is prepared by wetlaid techniques.

Fibers suitable for use in preparing the nonwoven fibrous porous matrix are usually pulpable or extrudable fibers such as those that are stable to radiation and/or to a variety of solvents. Optionally, at least some of the polymeric fibers can be selected to exhibit a degree of hydrophilicity. Useful fibers include polymeric fibers, inorganic fibers, and combinations thereof. More particularly, the fibers include a plurality of different types of fibers, including polyolefin fibers and fiberglass fibers.

Suitable polymeric fibers include those made from natural polymers (those derived from animal or vegetable sources) and/or synthetic polymers, including thermoplastic and solvent-dispersible polymers. Useful polymers include polyolefins (for example, poly(ethylene) (e.g., low density polyethylene, medium density polyethylene, high density polyethylene, etc.), polypropylene, poly(1-butene), copolymers of ethylene and propylene, alpha olefin copolymers such as copolymers of ethylene or propylene with 1-butene, 1-hexene, 1-octene, and 1-decene such as poly(ethylene-co-1-butene), poly(ethylene-co-1-butene-co-1-hexene), and the like); polylactic acid; poly(isoprenes); poly(butadienes); polyamides (for example, nylon 6, nylon 6,6, nylon 6,12, poly(iminoadipoyliminohexamethylene), poly(iminoadipoyliminodecamethylene), polycaprolactam, and the like); polyimides (for example, poly(pyromellitimide) and the like); polyethers; poly(ether sulfones) (for example, poly (diphenylether sulfone), poly(diphenylsulfone-co-diphenylene oxide sulfone), and the like); poly(sulfones); poly (vinyl esters) such as poly(vinyl acetates); copolymers of vinyl acetate (for example, poly(ethylene-co-vinyl acetate), copolymers in which at least some of the acetate groups have been hydrolyzed to provide various poly(vinyl alcohols) including poly(ethylene-co-vinyl alcohol), and the like); poly(phosphazenes); poly(vinyl ethers); poly(vinyl alcohols); polyaramids (for example, para-aramids such as poly (paraphenylene terephthalamide) and fibers sold under the trade designation "KEVLAR" by DuPont Co., Wilmington, Del., pulps of which are commercially available in various grades based on the length of the fibers that make up the pulp such as, for example, "KEVLAR 1F306" and "KEVLAR 1F694", both of which include aramid fibers that are at least 4 mm in length; and the like); wool; silk; cellulosic polymers (for example, cellulose, cellulose derivatives such as rayon, and the like); acrylic polymers (for example, polyacrylonitrile); polyesters (for example, polyethylene terephthalate); fluorinated polymers (for example, poly(vinyl fluoride), poly(vinylidene fluoride), copolymers of vinylidene fluoride such as poly(vinylidene fluoride-co-hexafluoropropylene), copolymers of chlorotrifluoroethylene such as poly(ethylene-co-chlorotrifluoroethylene), and the like); chlorinated polymers; poly(carbonates); and the like; and combinations thereof. In certain embodiments, the polymeric fibers comprise a polyolefin, a polysulfone, a polyamide, or a combination thereof.

Suitable inorganic fibers include those that contain at least one inorganic material selected from glasses, ceramics, and combinations thereof. These fibers are often added to provide strength to the fibrous porous matrix. For example, porous matrix layers containing inorganic fibers are often capable of being bent, folded, or pleated without breaking apart. Useful inorganic fibers include, for example, fiberglass (for example, E-glass, S-glass, and the like), ceramic fibers (for example, fibers made of metal oxides (such as alumina), silicon carbide, boron nitride, boron carbide, and the like), and combinations thereof. Useful ceramic fibers can be at least partially crystalline (exhibiting a discernible X-ray powder diffraction pattern or containing both crystalline and amorphous (glass) phases). In some applications, the inorganic fibers include fiberglass.

To facilitate entrapment of the guanidine-functionalized perlite particles and/or to ensure a high surface area, the fibers used to form the nonwoven, fibrous porous matrix often contain at least one fibrillated fiber (for example, in the form of a main fiber surrounded by many smaller attached fibrils). The main fiber generally can have a length in the range of 0.5 millimeters to 5 millimeters and a diameter in a range of 1 micrometer to 20 micrometers. The fibrils typically can have a sub-micrometer diameter. In many embodiments, the fibrillated fibers are prepared from a polyolefin such as poly(ethylene) or polypropylene, or from an acrylic polymer such as polyacrylonitrile.

Suitable polymeric fibers further include bi-component fibers, which typically assist in binding all of the matrix fibers together due to a difference in melting point of one of the materials in the bi-component fiber. Bi-component fibers can have, for example, a core-sheath structure, a side-by-side structure, an islands-in-the-sea structure, or a segmented-pie structure, or the like. An example side-by-side bi-component fiber is the polyolefin thermally bonded bi-component fiber that is commercially available from Chisso Corporation (Osaka, Japan) under the trade designation CHISSO (for example, CHISSO ES). An example core-sheath bi-component fiber is commercially available from Unitika Ltd. (Osaka, Japan) under the trade designation MELTY (for example, MELTY 4080) and those commercially available from Minifibers, Inc. (Johnson City, Tenn.) made of ethyl vinyl acetate (sheath) and polypropylene (core), or made of a co-polyester of polyester and polyethylene terephthalate (PET) (sheath) and polyester (core).

The nonwoven fibrous porous matrix contains a plurality of different types of fibers. In some embodiments, the porous matrix can be formed using three, four, or even more different types of fibers. For example, a fiberglass fiber can be added for strength and integrity, while fibrillated poly(ethylene) can be added for entrapment of the particulates. Additionally, nylon fibers provide hydrophilic character while fibrillated poly(ethylene) fibers provide hydrophobic character to the porous matrix. If fibrillated and non-fibrillated fibers are used in combination, the weight ratio of fibrillated fibers to non-fibrillated fibers is often at least 1:2, at least 1:1, at least 2:1, at least 3:1, at least 5:1, or even at least 8:1. In some embodiments, mixtures of hydrophobic and hydrophilic polymeric fibers are used. For example, the fibrous porous matrix can include a mixture of hydrophobic fibers such as polyolefins plus hydrophilic fibers such as polysulfones. In some specific examples, the polymeric fibers include polyolefin fibers, bi-component fibers, and fiberglass fibers.

In certain embodiments, the fibrous porous matrix is free of polyamide fibers. It has been discovered that the inclusion of nylon fibers in the fibrous porous matrix can result in lower luminescence than the fibrous porous matrix without the nylon fibers for a bioluminescent ATP detection method.

Preferably, the fibers used to form the nonwoven fibrous porous matrix are uncrimped. In contrast to uncrimped fibers, crimped fibers may be identified as displaying repeating features (as manifested e.g., in a wavy, jagged, sinusoidal, etc., appearance of the fiber), by having a helical appearance (e.g., particularly in the case of crimped fibers obtained by thermal activation of bi-component fibers), and the like, and are readily recognizable by those of ordinary skill in the art. Exemplary crimped fibers are described in U.S. Pat. No. 4,118,531 to Hauser and U.S. Pat. No. 5,597,645 to Pike et al., and CA Patent 2612854 to Sommer et al.

The fibers used to form the nonwoven fibrous porous matrix can be of a length and diameter that can provide a porous matrix having sufficient structural integrity and sufficient porosity for a particular application (for example, passing a fluid sample through the matrix). The fiber lengths are often at least about 0.5 millimeter, at least 1 millimeter, at least 2 millimeters, at least 3 millimeters, at least 4 millimeters, at least 6 millimeters, at least 8 millimeters, at least 10 millimeters, at least 15 millimeters, or at least 20 millimeters, and up to 50 millimeters, up to 40 millimeters, up to 30 millimeters, or up to 25 millimeters. The diameter of the fibers can be, for example, at least 10 micrometers, at least 20 micrometers, or at least 30 micrometers. The fiber lengths and diameters will vary depending upon factors such as the nature of the fiber and the type of application.

The nonwoven fibrous porous matrix often includes a mixture of polyolefin fibers, glass fibers, and bi-component fibers. In some particular embodiments, the nonwoven fibrous porous matrix contains a mixture of fibrillated polyethylene fibers, glass fibers, and sheath-core bi-component fibers. In some examples, the nonwoven fibrous porous matrix contains 40 to 80 weight percent fibrillated polyethylene fibers, 5 to 20 weight percent glass fibers, and 5 to 20 weight percent bi-component fibers. In some examples, the nonwoven fibrous porous matrix contains 40 to 80 weight percent fibrillated polyethylene fibers, 10 to 30 weight percent nylon fibers, 5 to 20 weight percent glass fibers, and 5 to 20 weight percent bi-component fibers. In other examples, the nonwoven, fibrous porous matrix contains 50 to 70 weight percent fibrillated polyethylene fibers, 5 to 15 weight percent glass fibers, and 5 to 20 weight percent bi-component fibers. In still other examples, the fibrous porous matrix contains 55 to 65 weight percent fibrillated polyethylene fibers, 0 to 20 weight percent nylon fibers, 5 to 15 weight percent glass fibers, and 10 to 20 weight percent bi-component fibers.

As noted above, the fibrous porous matrix consists essentially of inorganic fibers and polymeric fibers. Accordingly, in most embodiments, the fibrous porous matrix contains only fibers. For example, at least 90 weight percent, at least 95 weight percent, at least 98 weight percent, at least 99 weight percent, or at least 99.5 weight percent of a dry fibrous porous matrix is fibers. In certain embodiments, the nonwoven article comprises a thickness of at least 0.1 millimeters, or at least 0.15 millimeters, or at least 0.2 millimeters, or at least 0.3 millimeters, or at least 0.4 millimeters, or at least 0.5 millimeters, or at least 0.6 millimeters. The nonwoven article usually comprises a thickness of up to 1 millimeter, or up to 0.9 millimeters, or up to 0.8 millimeters, or up to 0.7 millimeters, or up to 0.55 millimeters. Stated differently, the nonwoven article may comprise a thickness of between 0.15 millimeters and 1 millimeter, or between 0.15 millimeters and 0.8 millimeters, or between 0.1 millimeters and 0.7 millimeters. In certain embodiments, a nonwoven article having a thickness towards the lower end of the thickness range is selected to minimize interference with detection of the microorganisms and/or cellular analytes, such as decreasing time required for a reagent to diffuse into the nonwoven article, or decreasing blockage of a generated detection signal.

The nonwoven article typically includes both the fibrous porous matrix and guanidine-functionalized perlite particles distributed within the fibrous porous matrix. In most embodiments, the nonwoven article contains at least 10 weight percent guanidine-functionalized perlite particles based on a total dry weight of the nonwoven article. If the amount of the guanidine-functionalized perlite particles is lower than about 10 weight percent, the nonwoven article may not contain enough guanidine-functionalized perlite particles to effectively capture microorganisms or cellular analytes from a fluid sample. In some examples, the nonwoven article contains at least 15 weight percent, at least 20 weight percent, at least 25 weight percent, or at least 30 weight percent guanidine-functionalized perlite particles based on a total dry weight of the nonwoven article.

On the other hand, the nonwoven article usually contains no greater than 55 weight percent guanidine-functionalized perlite particles based on the total dry weight of the nonwoven article. If the amount of the guanidine-functionalized perlite particles is greater than about 55 weight percent, the nonwoven article may contain an insufficient amount of the fibrous porous matrix. That is, the strength of the nonwoven article may be insufficient to hold together when employed to capture microorganism strains and/or target cellular analytes. In some examples, the nonwoven article contains no greater than 50 weight percent, no greater than 45 weight percent, or no greater than 40 weight percent guanidine-functionalized perlite particles based on a total weight of the nonwoven article.

Stated differently, the nonwoven article often contains 10 to 55 weight percent guanidine-functionalized perlite particles and 45 to 90 weight percent fibrous porous matrix, 15 to 50 weight percent guanidine-functionalized perlite particles and 50 to 85 weight percent fibrous porous matrix, 20 to 50 weight percent guanidine-functionalized perlite particles and 50 to 80 weight percent fibrous porous matrix, 20 to 45 weight percent guanidine-functionalized perlite particles and 55 to 80 weight percent fibrous porous matrix, 25 to 40 weight percent guanidine-functionalized perlite particles and 60 to 75 weight percent fibrous porous matrix, or 30 to 40 weight percent guanidine-functionalized perlite particles and 60 to 70 weight percent fibrous porous matrix. The amounts are based on the total dry weight of the nonwoven article.

In many embodiments, the nonwoven article (when dry) contains only guanidine-functionalized perlite particles and fibrous porous matrix. For example, the nonwoven article contains at least 90 weight percent, at least 95 weight percent, at least 98 weight percent, at least 99 weight percent, or at least 99.5 weight percent combined guanidine-functionalized perlite particles and fibrous porous matrix when dry.

In one specific method, a nonwoven article is prepared using a wet laying or "wetlaid" process. In this process, a dispersion is formed that contains (a) a plurality of fibers, (b) a plurality of guanidine-functionalized perlite particles, (c) polymeric binder fibers, (d) and a dispersing liquid such as water, a water-miscible organic solvent, or a mixture thereof. The fibers and guanidine-functionalized perlite particles can be dispersed together in the dispersing liquid. In some embodiments, the fibers (for example, hydrophobic fibers) have additives, surface treatments, or chemical groups that facilitate dispersion of the fibers in the dispersion liquid. For example, polyolefin-based fibers can have maleic anhydride or succinic anhydride functionality, or, during the melt-processing to prepare polyolefin-based fibers, a suitable surfactant can be added.

The wetlaid process additionally includes dewatering, followed by heating to finish the dewatering and optionally to bind some of the fibers together.

One or more adjuvants or additives are optionally used in preparing this type of nonwoven article. Useful adjuvants include process aids, surfactants, solvents, dispersants, flocculating aids, retention aids, or other materials that can enhance the overall performance of the resulting nonwoven article. When used, the amounts of such adjuvants can be present, for example, in an amount up 5 weight percent, up to 4 weight percent, up to 3 weight percent, up to 1 weight percent, or up to 0.5 weight percent based on a total dry weight of the nonwoven article (for example, fibers and guanidine-functionalized perlite particles). The total amount of adjuvants is typically selected to be as low as possible so as to maximize the amount of guanidine-functionalized perlite particles that can be included in the nonwoven article.

In one more specific wetlaid process, the fibers (for example, chopped fibers) can be blended in a container in the presence of the dispersing liquid (for example, water, a water-miscible organic solvent such as an alcohol, or a mixture thereof) to form a slurry. After formation of the slurry, the guanidine-functionalized perlite particles and an optional precipitation agent (for example, a pH adjusting agent such as alum) can be added to the slurry.

When the wetlaid process is carried out by using handsheet methods known in the art, the order of addition of the components (i.e., fibers and guanidine-functionalized perlite particles) to the dispersion has not been found to significantly affect the ultimate performance of the nonwoven article. After formation, the dispersion mixture can be poured into a mold, the bottom of which can be covered by a screen. The dispersing liquid can be allowed to drain from the mixture (in the form of a wet sheet) through the screen. After sufficient liquid has drained, the wet sheet generally can be removed from the mold and dried by pressing, heating, or a combination of the two. Generally pressures are in a range of about 300 to about 600 kPa. Temperatures in a range of 90° C. to 200° C., in a range of 100° C. to 175° C., in a range of 100° C. to 150° C., or in a range of 90° C. to 120° C. can be used for drying the wet sheet. Drying often removes all or most of the dispersing liquid (for example, up to 85 weight percent, up to 90 weight percent, up to 95 weight percent, up to 98 weight percent, or up to 99 weight percent of the dispersing liquid based on the amount of dispersing liquid added to form the dispersion).

The resulting nonwoven article is a dry sheet having an average thickness of at least 0.1 millimeter, at least 0.2 millimeters, at least 0.5 millimeters, at least 0.8 millimeters, at least 1 millimeter, at least 2 millimeters, at least 4 millimeters, or at least 5 millimeters. The average thickness is often up to 20 millimeters, up to 15 millimeters, up to 12 millimeters, or up to 10 millimeters. Calendering can be used to provide additional pressing or fusing, if desired, of the dry sheet. The basis weight of the nonwoven article (in the form of sheet material) can be in the range of about 100 to about 350 grams per square meter ($g/m^2$), preferably, in the range of about 200 to about 300 $g/m^2$, such as about 250 $g/m^2$.

In the nonwoven article, the guanidine-functionalized perlite particles can be entrapped in the fibrous porous matrix through either chemical interactions (for example, chemical bonding) or physical interactions (for example, adsorption or mechanical entrapment), depending upon the nature of the fibers that are utilized. The guanidine-functionalized perlite particles are often preferably distributed essentially uniformly throughout the fibrous porous matrix within the nonwoven article.

Generally the average pore size of the dry nonwoven article can be in a range of 0.1 to 10 micrometers, as measured by scanning electron microscopy (SEM). Void volumes in the range of 20 to 80 volume percent or in a range of 40 to 60 volume percent can be useful. The porosity of the dry nonwoven article can be modified (increased) by using fibers of larger diameter or stiffness in the fiber mixture.

In a third aspect, a laminated article is provided. The laminated article includes a first substrate and a second substrate sealed to the first substrate along at least a portion of a perimeter of the first substrate. The laminated article further includes a plurality of guanidine-functionalized perlite particles disposed between the first substrate and the second substrate.

Substrates that are suitable for laminated articles of the present disclosure include a spunbond polypropylene, a spunbond blend of polyamide and polyester, a spunbond polyamide, a spunbond polyethylene, a spunbond polyester, a spunbond polybutylene terephthalate (PBT), a spunbond polypropylene, a melt-blown web, a staple web, and most preferably a spunbond polypropylene or a spunbond blend of polyamide and polyester. Preferably, each of the first substrate and the second substrate are selected from materials that shed few or no fibers, such that the turbidity of a fluid sample passed through the laminated article is not detectably increased as compared to the turbidity of the fluid sample prior to being passed through the laminated article, or passes the Turbidity Test described below. The first substrate and the second substrate are independently selected from suitable materials, but often include the same material. It is emphasized that the terminology of "first" and "second" substrates is used purely for convenience of description; in certain embodiments, the first substrate and the second substrate are portions of a single continuous substrate, whereas in alternate embodiments the first substrate and the second substrate are individual, separate, substrates. One example of the first substrate and the second substrate being portions of a single continuous substrate, for instance, is a substrate folded in half wherein one half provides the first substrate while the other half provides the second substrate.

To allow flow of a liquid (e.g., a fluid sample) through the thickness of the laminated article, each of the first substrate and the second substrate is fluid permeable. In many applications, fluids comprising water (e.g., aqueous solutions or dispersions) will be passed through the laminated article, thus optionally at least one of the first substrate and the second substrate comprise a hydrophilized substrate to improve wettability and penetration of the liquid through one or both substrates. Hydrophilization is well known to the skilled practitioner, and may be performed using plasma treatment, for instance (see, e.g., U.S. Pat. No. 4,772,488).

Characteristics of spunbond materials typically correlated to porosity include the basis weight of a unit area of the material and the diameter of the individual fibers of which the spunbond materials are composed. Suitable substrates for laminated articles according to the present disclosure include one or more spunbond materials comprising a gram per square meter basis weight (gsm) of at least about 10, 25, 40, 55, 60, or even 65 gsm up to about 75, 80, 90, 100, 140, 180, or even 200 gsm. For example, in certain aspects, the first substrate and the second substrate independently include a spunbond material comprising a gsm of 10 to 200 gsm, preferably 55 to 100 gsm, and most preferably 60 to 100 gsm, inclusive. In certain aspects, the first substrate and the second substrate independently comprise a spunbond material comprising a fiber diameter of at least about 10 micrometers (µm), 11, 12, 13, 14, or even 15 µm up to about 17, 18, 19, 20, 22, 24, 26, 28, or even 30 µm. For example, in certain aspects, the first substrate and the second substrate independently comprise a spunbond material comprising a fiber diameter of 10 to 30 µm, and preferably 10 to 18 µm, 12 to 20 µm, or 14 to 22 µm, inclusive.

Laminated articles of the present disclosure include a seal to secure the first substrate to the second substrate. In particular, the second substrate is sealed to the first substrate along at least a portion of the perimeter of the substrate. As used herein, the term "perimeter" means the border or outer boundary of a substrate, including all of the area within about 10% of the distance of the furthest edge of the border or outer boundary inward towards the center of the substrate. For instance, if a substrate comprises a circular shape having a radius of 10 centimeters (cm), the perimeter includes any of the area from the outer edge to 1 cm in from the outer edge toward the center of the circular shape. Alternatively, if a substrate comprises a rectangle (e.g., polygon) shape having a length of 40 cm and a height of 20 cm, the perimeter includes any of the area from the outer edges of the short ends to 4 cm in towards the center point of the rectangle and from the outer edges of the long ends to 2 cm in towards the center point of the rectangle. Typically, the second substrate is sealed to the first substrate along at least about 75%, or 85%, or 90% of the perimeter of the first substrate, and up to about 95%, or 98%, or 100% of the perimeter of the first substrate. In addition to the sealing along at least a portion of the perimeter of the first substrate, point bonding (or pin bonding) of discreet points inward of the perimeter of the first substrate is optionally also employed. An advantage of performing point bonding is providing further stability of the guanidine-functionalized perlite particles remaining where they were originally disposed between the first and second substrates.

Sealing of the first substrate to the second substrate may be accomplished by various suitable methods known in the art, including for example and without limitation, ultrasonic sealing, heat sealing, adhesive sealing, stitching, or a combination thereof. Ultrasonic sealing may be a preferred method, and is typically performed at an energy setting of at least about 150 joules (J), or 175 J, or 200 J, or even 225 J, up to about 200 J, 225 J, or even 250 J, for example 150 J to 250 J, inclusive. In certain embodiments, the ultrasonic sealing simultaneously seals and cuts the laminated article in a single step, eliminating the need for individually separating the laminated article from the substrate material.

Laminated articles of the present disclosure can be prepared by a process comprising (a) providing a plurality of the above-described guanidine-functionalized perlite particles; (b) providing the above-described first substrate; (c) providing the above-described second substrate; (d) disposing the guanidine-functionalized perlite particles between the first substrate and the second substrate; and (e) sealing the second substrate to the first substrate along at least a portion of a perimeter of the first substrate (as described above).

In a fourth aspect, a method of detecting microorganisms or target cellular analytes in a fluid sample is provided. The method includes providing a laminated article according to the third aspect (as described above) and providing a fluid sample suspected of containing at least one microorganism strain or target cellular analyte. The method further includes contacting the fluid sample with the laminated article such that at least a portion of the at least one microorganism strain or target cellular analyte is bound to the laminated article and detecting the presence of the at least one bound microorganism strain or bound target cellular analyte.

The methods according to the present disclosure can be carried out by any of various known or hereafter-developed methods of providing contact between two materials. For example, the laminated article or nonwoven article can be added to the fluid sample, or the fluid sample can be added to the articles. For instance, sample can be passed over or through (preferably, through) the laminated article or nonwoven article. For the nonwoven article, the contacting is optionally carried out in a manner such that the sample passes through a pore of the fibrous porous matrix (such as a through pore). For the laminated article, the contacting is optionally carried out in a manner such that the sample passes through the first substrate, past at least one guanidine-functionalized perlite particle, and the second substrate. In an embodiment of the present disclosure, a filtration device is includes a container having inlet and outlet ports for liquid passage, and a laminated article or nonwoven article of the present disclosure contained within the container.

Contacting can be carried out for a desired period (for example, for sample volumes of several liters or for processes involving multiple passes through a laminated article or nonwoven article, up to about 60 minutes of contacting can be useful, or about 15 seconds to about 30 minutes, or about 15 seconds to about 15 minutes, or about 15 second to about 10 minutes, or about 15 seconds to about 5 minutes, or even about 15 seconds to about 2 minutes).

Contacting can be effected by passing a sample at least once (preferably, only once) through a laminated article or nonwoven article (for example, by gravity, by vacuum, or by pumping). Essentially any type of pump (for example, a peristaltic pump) or other equipment for establishing a pressure differential across a sample of the nonwoven article or laminated article contained in a suitable container having inlet and outlet ports for liquid passage (for example, a syringe or plunger) can be utilized. Useful flow rates will vary, depending upon such factors as the nature of the fluid sample matrix and the particular application. Advantageously, the nonwoven articles and laminated articles of the present disclosure require only a very low pressure differential across the articles to effectively pass a fluid sample through the articles. This characteristic is particularly beneficial in environments, for instance, when no or low power pumps are available for processing a fluid sample, or in dealing with complex sample matrices such as industrial water samples. In an embodiment of the present disclosure, the contacting comprises passing the fluid sample through the nonwoven article or laminated article at a pressure of 14.7 pounds per square inch (psi) (101.3 kilopascals (kPa)) or less, or 4.0 pounds per square inch (psi) (27.58 kilopascals (kPa)) or less, or 3.0 psi (20.68 kPa), or 2.0 psi (13.79 kPa), or 1.0 psi (6.9 kPa), or 0.9 psi (6.21 kPa), or 0.8 psi (5.52 kPa), or 0.7 psi (4.83 kPa), or 0.6 psi (4.14 kPa), or even 0.5 psi (3.45 kPa) or less, and at a pressure of at least 0.4 psi (2.76 kPa), or at least 0.5 psi (3.45 kPa).

Advantageously, the laminated article of the present disclosure sufficiently encapsulates the guanidine-functionalized perlite particles and the first and second substrates maintain their integrity, such that the laminated article provides a turbidity of less than 0.2 nephelometric turbidity units (NTU), or less than 0.15 NTU, or less than 0.10 NTU, according to the Turbidity Test. The Turbidity Test is an indicator of how much (if any) material (e.g., fibers, and/or particles) from the guanidine-functionalized perlite particles and/or the substrates could potentially be shed during use of the laminated article. The Turbidity Test is significant in particular when the fluid sample contacted with the laminated article is intended to be used following the contact, for instance, when the fluid sample is potable water. The Turbidity Test is based on the "Standard for Hygienic Safety Evaluation of Equipment and Protective Materials in Drinking Water," (standard number GB/T 17219-1998) and is as follows: A 47 mm disk of a laminated sample is placed in a 2.5 liter vacuum filtration apparatus (with a side arm) and flushed continuously with DI water for 30 minutes. The sample is then removed and placed in a glass jar containing 70 mL DI water for 24 hours. Water sample aliquots are analyzed for turbidity using a turbidimeter, such as a MICRO 100 TURBIDIMETER (available from HF scientific, Fort Myers, Fla.). Out of the 70 mL sample 2 samples of 25 mL are used for turbidity measurements. A volume of 70 mL of DI water serves as control.

In a fifth aspect, another method of detecting microorganisms or target cellular analytes in a fluid sample is provided. The method includes providing a plurality of guanidine-functionalized perlite particles according to the second aspect (as described above) and providing a fluid sample suspected of containing at least one microorganism strain or target cellular analyte. The method further includes contacting the fluid sample with the plurality of guanidine-functionalized perlite particles such that at least a portion of the at least one microorganism strain or target cellular analyte is bound to the guanidine-functionalized perlite particles and detecting the presence of the at least one bound microorganism strain or bound target cellular analyte.

Contacting the fluid sample with the plurality of guanidine-functionalized perlite particles typically comprises dispersing at least a portion of the particles in the fluid sample. Optionally, the guanidine-functionalized perlite particles and the fluid sample are combined (using any order of addition) in any of a variety of containers (optionally but preferably, a capped, closed, or sealed container; more preferably, a capped test tube, bottle, or jar). Suitable containers for use in carrying out the process of the invention will be determined by the particular sample and can vary widely in size and nature. For example, the container can be small, such as a 10 microliter container (for example, a test tube) or larger, such as a 100 milliliter to 3 liter container (for example, an Erlenmeyer flask or a polypropylene large-mouth bottle). The container and any other apparatus or additives that contact the fluid sample directly can be sterilized (for example, by controlled heat, ethylene oxide gas, hydrogen peroxide, or radiation) prior to use, in order to reduce or prevent any contamination of the sample that might cause detection errors. The amount of guanidine-functionalized perlite particles that is sufficient to capture or concentrate the microorganisms and/or cellular analytes of a particular sample for successful detection will vary (depending upon, for example, the nature and form of the concentration agent and sample volume) and can be readily determined by one skilled in the art. For example, 10 milligrams of guanidine-functionalized perlite particles per milliliter of sample can be useful for some applications.

If desired, contacting can be effected by passing the guanidine-functionalized perlite particles at least once through a fluid sample (for example, by relying upon gravitational settling over a period of, for example, about 10 minutes). Contact can be enhanced by mixing (for example, by stirring, shaking, or use of a rocking platform) such that the particles of guanidine-functionalized perlite repeatedly pass or settle through a substantial portion of the fluid sample. For small volumes on the order of microliters (typically less than 0.5 milliliter), mixing can be rapid such as by vortexing or "nutation," for example as described in U.S. Pat. No. 5,238,812 (Coulter et al.). For larger volumes on the order of greater than or equal to 0.5 milliliters (typically 0.5 milliliter to 3 liters), mixing can be achieved by gently tumbling the particulate concentration agent and the sample in an "end over end" fashion, for example as described in U.S. Pat. No. 5,576,185 (Coulter et al.). Such tumbling can be accomplished, for example, by means of a device configured to hold a test tube or other type of reaction vessel and to slowly rotate the test tube or vessel in an "end over end" manner. Contacting can be carried out for a desired period (for example, for sample volumes of about 100 milliliters or less, up to about 60 minutes of contacting can be useful; preferably, about 15 seconds to about 10 minutes or longer; more preferably, about 15 seconds to about 5 minutes).

Thus, mixing (for example, agitation, rocking, or stirring) and/or incubation (for example, at ambient temperature) are optional but preferred, in order to increase microorganism contact with the guanidine-functionalized perlite particles. In certain embodiments, contacting includes both mixing (for example, for about 15 seconds to about 5 minutes) and incubating (for example, for about 3 minutes to about 30 minutes) a microorganism-containing fluid sample with guanidine-functionalized perlite particles. If desired, one or more additives (for example, lysis reagents, bioluminescence assay reagents, nucleic acid capture reagents (for example, magnetic beads), microbial growth media, buffers (for example, to disperse or extract a solid sample), microbial staining reagents, washing buffers (for example, to wash away unbound material), elution agents (for example, serum albumin), surfactants (for example, TRITON X-100 nonionic surfactant available from Union Carbide Chemicals and Plastics, Houston, Tex.), mechanical abrasion/elution agents (for example, glass beads), and the like) can be included in the combination of guanidine-functionalized perlite particles and fluid sample.

Optionally, the method further comprises segregation of the resulting microorganism-bound guanidine-functionalized perlite particles. Such segregation preferably can be achieved by relying, at least in part, upon gravitational settling (gravity sedimentation; for example, over a time period of about 5 minutes to about 30 minutes). In some cases, however, it can be desirable to accelerate segregation (for example, by centrifugation or filtration) or to use combinations of any of the segregation methods.

The method can optionally further comprise separating the resulting microorganism-bound guanidine-functionalized perlite particles and the fluid sample. This can involve removal or separation of the supernatant that results upon segregation. Separation of the supernatant can be carried out by numerous methods that are well-known in the art (for example, by decanting or siphoning, so as to leave the microorganism-bound guanidine-functionalized perlite particles at the bottom of the container or vessel utilized in carrying out the process). The method can be carried out manually (for example, in a batch-wise manner) or can be automated (for example, to enable continuous or semi-continuous processing).

The fluid sample can be provided from a variety of different types of samples, including, but not limited to, medical, environmental, food, feed, clinical, and laboratory samples, and combinations thereof. Medical or veterinary samples can include, for example, cells, tissues, or fluids from a biological source (for example, a human or an animal) that are to be assayed for clinical diagnosis. Environmental samples can be, for example, from a medical or veterinary facility (e.g., rinsate from cleaning medical supplies, such as lumened devices), an industrial facility (e.g., produced water and cooling tower water), soil, a water source, a food preparation area (food contact and non-contact areas), or a laboratory. Examples of samples that can be used include beverages (for example, juices, beers, or carbonated beverages), water (including potable water), biological fluids, and the like.

Fluid samples obtained in the form of a liquid or in the form of a dispersion or suspension of solid in liquid can be used directly, or can be concentrated (for example, by centrifugation) or diluted (for example, by the addition of a buffer (pH-controlled) solution). Samples in the form of a solid or a semi-solid can be extracted, if desired, by a method such as, for example, washing or rinsing with, or suspending or dispersing in, a fluid medium (for example, a buffer solution). Samples can be taken from surfaces (for example, by swabbing or rinsing). Preferably, the sample is at least a fluid (for example, a liquid, a gas, or a dispersion or suspension of solid or liquid in liquid or gas).

Sample volume can vary, depending upon the particular application. For example, for a diagnostic or research application, the volume of the fluid sample can be as small as in the microliter range (for example, 10 microliters or greater). When a filtering process is used for potable water safety testing, the volume of the sample can typically be in the milliliter to liter range (for example, 100 milliliters to 3 liters). In industrial or residential applications, the volume can be up to tens of thousands of liters.

If desired, one or more additives (for example, lysis reagents, bioluminescence assay reagents, nucleic acid capture reagents (for example, magnetic beads), microbial growth media, buffers (for example, to moisten a solid sample), microbial staining reagents, washing buffers (for example, to wash away unbound material), elution agents (for example, serum albumin), surfactants (for example, "TRITON X-100" nonionic surfactant available from Union Carbide Chemicals and Plastics, Houston, Tex.), adsorption buffers, and the like can be included in a combination of the fluid sample and the guanidine-functionalized perlite particles, nonwoven article, or laminated article after contacting.

A variety of microorganisms can be concentrated and detected by using the nonwoven articles and methods of the disclosure, including, for example, bacteria, fungi, yeasts, protozoans, viruses (including both non-enveloped and enveloped viruses), fungal spores, bacterial endospores (for example, *Bacillus* (including *Bacillus anthracia*, *Bacillus cereus*, and *Bacillus subtilis*) and *Clostridium* (including *Clostridium botulinum*, *Clostridium difficile*, and *Clostridium perfringens*)), and the like, and combinations thereof, such as gram-negative bacteria, gram-positive bacteria, yeasts, fungi, and combinations thereof. Target cellular analyte that can be concentrated and detected by using the methods of the disclosure include nucleic acids, proteins, adenosine triphosphate (ATP), or combinations thereof.

The methods optionally further comprise passing the fluid sample through a coarse filter prior to the contacting the fluid sample with guanidine-functionalized perlite particles, a nonwoven article, or a laminated article. The use of such a filter can remove particulates from the fluid sample that might otherwise clog the article or interfere with the contacting. Suitable coarse filters include for example and without limitation, filters comprising pore sizes of at least 1 micrometer, at least 5 micrometers, at least 10 micrometers, at least 25 micrometers, or at least 50 micrometers.

In certain embodiments, the method further comprises washing the at least one microorganism strain- or target cellular analyte-bound laminated article, nonwoven article, or guanidine-functionalized perlite particles, prior to detection. It has been discovered that contaminants such as residual sample matrix can be removed from without significant loss of the bound or captured microorganisms and/or cellular analytes. In certain embodiments, washing includes for instance and without limitation, rinsing with sterile deionized water or bottled drinking water, or rinsing with aqueous salt or buffer solutions. Washing the laminated article, nonwoven article, or guanidine-functionalized perlite particles tends to remove components that could otherwise interfere with detecting the presence of the bound microorganisms and/or cellular analytes, depending on the particular detection method employed.

In certain embodiments, detecting the bound microorganism strain- or target cellular analyte-bound comprises placing the guanidine-functionalized perlite particles, the laminated article, or the nonwoven article in a receptacle that comprises a material through which a detection signal can be detected, wherein the receptacle contains at least one reagent. For instance, placing the microorganism strain- or target cellular analyte-bound material in contact with a reagent optionally includes placing the guanidine-functionalized perlite particles, the laminated article, or the nonwoven article in a receptacle configured to be operationally connected to a luminometer, wherein the receptacle contains at least one reagent. Hence, in such an embodiment, detection is facilitated by disposing the receptacle in the luminometer for measurement of light generated from reaction of the bound microorganism strain and/or target cellular analyte with at least one reagent. Similarly, the receptacle can be interfaced with other types of equipment depending on the particular detection method. In certain embodiments, placing the microorganism strain- or target cellular analyte-bound guanidine-functionalized perlite particles, laminated article, or nonwoven article in contact with a reagent includes pushing the material into a receptacle containing the at least one reagent. Nonlimiting examples of suitable receptacles, for instance receptacles containing at least one reagent, include the 3M CLEAN-TRACE Surface ATP Swab available from 3M Company (St. Paul, Minn.), the AQUASNAP ATP Water Test available from Hygiena (Camarillo, Calif.), the ACCUPOINT 2 ATP Sanitation Monitoring System available from Neogen Corporation (Lansing, Mich.), and the PRO-CLEAN Rapid Protein Residue Test available from Hygiena.

It has been discovered that microorganism strain and/or target cellular analyte can be detected without requiring removal from being captured by the guanidine-functionalized perlite particles, laminated article, or nonwoven article. The ability to detect microorganism strains and/or target cellular analytes attached to the guanidine-functionalized perlite particles, laminated article, or nonwoven article is advantageous because it decreases the number of required method steps as compared to methods in which the microorganism strains and/or target cellular analytes need to be eluted from a material prior to detection. Further, the guanidine-functionalized perlite particles, laminated article, or nonwoven article concentrates the microorganism strains and/or target cellular analytes into the volume of the material, which is typically significantly smaller than the volume of the fluid sample.

Microorganisms and/or cellular analytes that have been captured or bound (for example, by adsorption, absorption, or by sieving) by the guanidine-functionalized perlite particles, laminated article, or nonwoven article can be detected by essentially any desired method that is currently known or hereafter developed. Such methods include, for example, culture-based methods, microscopy (for example, using a transmitted light microscope or an epifluorescence microscope, which can be used for visualizing microorganisms tagged with fluorescent dyes) and other imaging methods, immunological detection methods, and genetic detection methods. The detection process following microorganism and/or cellular analyte capture optionally can include washing to remove sample matrix components, staining, boiling or using elution buffers or lysis agents to release cellular analyte from the nonwoven article, or the like.

Immunological detection is detection of an antigenic material derived from a target organism, which is commonly a biological molecule (for example, a protein or proteoglycan) acting as a marker on the surface of bacteria or viral particles. Detection of the antigenic material typically can be by an antibody, a polypeptide selected from a process such as phage display, or an aptamer from a screening process.

Immunological detection methods are well-known and include, for example, immunoprecipitation and enzyme-linked immunosorbent assay (ELISA). Antibody binding can be detected in a variety of ways (for example, by labeling either a primary or a secondary antibody with a fluorescent dye, with a quantum dot, or with an enzyme that can produce chemiluminescence or a colored substrate, and using either a plate reader or a lateral flow device).

Detection can also be carried out by genetic assay (for example, by nucleic acid hybridization or primer directed amplification). The captured or bound microorganisms can be lysed to render their genetic material (e.g., cellular analytes) available for assay. Lysis methods are well-known and include, for example, treatments such as sonication, osmotic shock, high temperature treatment (for example, from about 50° C. to about 100° C.), and incubation with an enzyme such as lysozyme, glucolase, zymolose, lyticase, proteinase K, proteinase E, and viral enolysins.

Many commonly-used genetic detection assays detect the nucleic acids of a specific microorganism, including the DNA and/or RNA. The stringency of conditions used in a genetic detection method correlates with the level of variation in nucleic acid sequence that is detected. Highly stringent conditions of salt concentration and temperature can limit the detection to the exact nucleic acid sequence of the target. Thus microorganism strains with small variations in a target nucleic acid sequence can be distinguished using a highly stringent genetic assay. Genetic detection can be based on nucleic acid hybridization where a single-stranded nucleic acid probe is hybridized to the denatured nucleic acids of the microorganism such that a double-stranded nucleic acid is produced, including the probe strand. One skilled in the art will be familiar with probe labels, such as radioactive, fluorescent, and chemiluminescent labels, for detecting the hybrid following gel electrophoresis, capillary electrophoresis, or other separation method.

Particularly useful genetic detection methods are based on primer directed nucleic acid amplification. Primer directed nucleic acid amplification methods include, for example, thermal cycling methods (for example, polymerase chain reaction (PCR), reverse transcriptase polymerase chain reaction (RT-PCR), and ligase chain reaction (LCR)), as well as isothermal methods and strand displacement amplification (SDA) (and combinations thereof; preferably, PCR or RT-PCR). Methods for detection of the amplified product are not limited and include, for example, gel electrophoresis separation and ethidium bromide staining, as well as detection of an incorporated fluorescent label or radio label in the product. Methods that do not require a separation step prior to detection of the amplified product can also be used (for example, real-time PCR or homogeneous detection).

Bioluminescence detection methods are well-known and include, for example, adensosine triphosphate (ATP) detection methods including those described in U.S. Pat. No. 7,422,868 (Fan et al.). Bioluminescence detection methods for ATP often include the known luciferin-luciferase system in which luciferase enzyme catalyzes the oxidation of luciferin in the presence of ATP and a divalent cation (such as magnesium or calcium). Other luminescence-based detection methods can also be utilized.

In many embodiments, detection comprises a culture-based detection method, an imaging detection method, a fluorescence-based detection method, a colorimetric detection method, an immunological detection method, a genetic detection method, a bioluminescence-based detection method, or a combination thereof.

Various embodiments are provided that include guanidine-functionalized perlite particles, a nonwoven article, a laminated article, and methods of detecting microorganisms or target cellular analytes in a fluid sample.

Embodiment 1 is a nonwoven article including a) a fibrous porous matrix and b) a plurality of guanidine-functionalized perlite particles enmeshed in the fibrous porous matrix.

Embodiment 2 is the nonwoven article of embodiment 1, wherein the fibrous porous matrix includes nonwoven fibers.

Embodiment 3 is the nonwoven article of embodiment 1 or embodiment 2, wherein the fibrous porous matrix includes polymeric fibers.

Embodiment 4 is the nonwoven article of any of embodiments 1 to 3, wherein the polymeric fibers include a polyamide, a polyolefin, a polysulfone, or a combination thereof.

Embodiment 5 is the nonwoven article of any of embodiments 1 to 4, wherein the fibrous porous matrix includes a fibrillated polyolefin polymeric fiber.

Embodiment 6 is the nonwoven article of any of embodiments 1 to 5, wherein the fibrous porous matrix further includes inorganic fibers.

Embodiment 7 is the nonwoven article of embodiment 6, wherein the inorganic fibers include glass fibers, ceramic fibers, or a combination thereof.

Embodiment 8 is the nonwoven article of any of embodiments 1 to 7, wherein the fibrous porous matrix consists essentially of nonwoven fibers.

Embodiment 9 is the nonwoven article of any of embodiments 1 to 8, wherein the nonwoven article includes 5 to 55 weight percent guanidine-functionalized perlite particles based on a total dried weight of the nonwoven article and 45 to 95 weight percent fibrous porous matrix based on the total dried weight of the nonwoven article.

Embodiment 10 is the nonwoven article of any of embodiments 1 to 9, wherein the nonwoven article includes 20 to 50 weight percent guanidine-functionalized perlite particles based on a total dried weight of the nonwoven article and 50 to 80 weight percent fibrous porous matrix based on the total dried weight of the nonwoven article.

Embodiment 11 is the nonwoven article of any of embodiments 1 to 10, wherein the fibrous porous matrix is a nonwoven fibrous layer including polymeric fibers and inorganic fibers.

Embodiment 12 is the nonwoven article of any of embodiments 1 to 11, wherein the fibrous porous matrix is a nonwoven fibrous layer and the guanidine-functionalized perlite particles are distributed throughout the nonwoven fibrous layer.

Embodiment 13 is the nonwoven article of embodiment 12, wherein the nonwoven fibrous layer includes polyolefin fibers and glass fibers.

Embodiment 14 is the nonwoven article of embodiment 13, wherein the inorganic fibers and polymeric fibers have an average length of less than 50 millimeters.

Embodiment 15 is the nonwoven article of any of embodiments 1 to 14, wherein the fibrous porous matrix is a nonwoven fibrous layer including uncrimped polymeric fibers.

Embodiment 16 is the nonwoven article of any of embodiments 1 to 15, wherein each of the guanidine-functionalized perlite particles includes a perlite particle that is modified with at least one silane having the formula $$X_{3-n}R^a{}_nSi\text{—}Y\text{-}G,$$

wherein:
n is 0, 1, or 2;
each $R^a$, if present, is independently an alkyl, aralkyl, or aryl;
Y is a divalent group comprising an alkylene having 2 to 20 carbons;
G is a guanidine group of the formula —NH—C(=NH)—NH$_2$; and
each X is independently alkoxy or acyloxy.

Embodiment 17 is the nonwoven article of embodiment 16, wherein the divalent group further comprises an arylene, oxy, —NH—, or a combination thereof.

Embodiment 18 is the nonwoven article of embodiment 16 or embodiment 17, wherein the divalent group is alkylene having 3 to 6 carbons.

Embodiment 19 is the nonwoven article of any of embodiments 16 to 18, wherein the guanidine group is the reaction product of a primary amine and an O-methylisourea salt.

Embodiment 20 is the nonwoven article of any of embodiments 16 to 19, wherein the linker is 3-aminopropyltrimethoxysilane.

Embodiment 21 is the nonwoven article of any of embodiments 14 to 18, wherein the ligand is the reaction product of one or more hydroxyl groups of the perlite particle with one or more reactive groups of a silane coupling agent moiety of the ligand.

Embodiment 22 is the nonwoven article of any of embodiments 1 to 19, wherein the guanidine-functionalized perlite particles have a surface nitrogen content of at least 2 atomic percent as measured by x-ray photoelectron spectroscopy (XPS).

Embodiment 23 is the nonwoven article of any of embodiments 1 to 20, wherein the guanidine-functionalized perlite particles have a surface nitrogen content of up to 12 atomic percent as measured by x-ray photoelectron spectroscopy (XPS).

Embodiment 24 is the nonwoven article of any of embodiments 1 to 21, wherein the fibrous porous matrix has a thickness of between 0.15 millimeters and 1 millimeter.

Embodiment 25 is a guanidine-functionalized perlite particle including a perlite particle that is modified with at least one silane having the formula $$X_{3-n}R^a{}_nSi\text{—}Y\text{-}G,$$

wherein:
n is 0, 1, or 2;
each $R^a$, if present, is independently an alkyl, aralkyl, or aryl;
Y is a divalent group comprising an alkylene having 2 to 20 carbons;
G is a guanidine group of the formula —NH—C(=NH)—NH$_2$; and
each X is independently alkoxy or acyloxy.

Embodiment 26 is the guanidine-functionalized perlite particle of embodiment 25, wherein the divalent group further comprises an arylene, oxy, —NH—, or a combination thereof.

Embodiment 27 is the guanidine-functionalized perlite particle of embodiment 25 or embodiment 26, wherein the divalent group is alkylene having 3 to 6 carbons.

Embodiment 28 is the guanidine-functionalized perlite particle of any one of embodiments 25 to 27, wherein the guanidine group is the reaction product of a primary amine and an O-methylisourea salt.

Embodiment 29 is the guanidine-functionalized perlite particle of any one of embodiments 25 to 28, wherein the linker is 3-aminopropyltrimethoxysilane.

Embodiment 30 is the guanidine-functionalized perlite particle of any one of embodiments 25 to 29, have a surface nitrogen content of at least 2 atomic percent as measured by x-ray photoelectron spectroscopy (XPS).

Embodiment 31 is the guanidine-functionalized perlite particle of any one of embodiments 25 to 30, have a surface nitrogen content of up to 12 atomic percent as measured by x-ray photoelectron spectroscopy (XPS).

Embodiment 32 is a laminated article including: a) a first substrate; b) a second substrate sealed to the first substrate along at least a portion of a perimeter of the first substrate; and c) a plurality of guanidine-functionalized perlite particles disposed between the first substrate and the second substrate.

Embodiment 33 is the laminated article of embodiment 32, wherein each of the guanidine-functionalized perlite particles includes a perlite particle that is modified with at least one silane having the formula $X_{3-n}R^a{}_n Si$—Y-G. In the formula, n is 0, 1, or 2 and each $R^a$, if present, is independently an alkyl, aralkyl, or aryl. In the formula, Y is a divalent group comprising an alkylene having 2 to 20 carbons, G is a guanidine group of the formula —NH—C(=NH)—$NH_2$, and each X is independently alkoxy or acyloxy.

Embodiment 34 is the laminated article of embodiment 32 or embodiment 33, wherein the first substrate and the second substrate are independently selected from a spunbond polypropylene, a spunbond polyamide, a spunbond blend of polyamide and polyester, a spunbond polyethylene, a spunbond polyester, a spunbond polybutylene terephthalate, and a spunbond polypropylene.

Embodiment 35 is the laminated article of any of embodiments 32 to 34, wherein the first substrate and the second substrate are independently selected from a spunbond polypropylene and a spunbond blend of polyamide and polyester.

Embodiment 36 is the laminated article of any of embodiments 32 to 35, wherein the first substrate and the second substrate independently include a spunbond material having a gram per square meter basis weight (gsm) of 10 to 200 gsm, inclusive.

Embodiment 37 is the laminated article of any of embodiments 32 to 36, wherein the first substrate and the second substrate independently include a spunbond material having a gram per square meter basis weight (gsm) of 55 to 100 gsm, inclusive.

Embodiment 38 is the laminated article of any of embodiments 32 to 37, wherein the first substrate and the second substrate independently include a spunbond material having a fiber diameter of 10 to 30 micrometers (μm), inclusive.

Embodiment 39 is the laminated article of any of embodiments 32 to 38, wherein the first substrate and the second substrate include the same material.

Embodiment 40 is the laminated article of any of embodiments 32 to 39, wherein the second substrate is sealed to the first substrate along up to 100% of the perimeter of the first substrate.

Embodiment 41 is the laminated article of any of embodiments 32 to 40, wherein the laminated article provides a turbidity of less than 0.2 nephelometric turbidity units (NTU) according to the Turbidity Test.

Embodiment 42 is the laminated article of any of embodiments 32 to 41, wherein the first substrate includes a circular shape or a polygon shape.

Embodiment 43 is the laminated article of any of embodiments 32 to 42, wherein at least one of the first substrate and the second substrate includes a hydrophilized substrate.

Embodiment 44 is the laminated article of any of embodiments 32 to 43, wherein each of the first substrate and the second substrate is liquid permeable.

Embodiment 45 is a method of detecting microorganisms or target cellular analytes in a fluid sample. The method includes a) providing a laminated article according to any one of embodiments 32 to 44; b) providing a fluid sample suspected of containing at least one microorganism strain or target cellular analyte; c) contacting the fluid sample with the laminated article such that at least a portion of the at least one microorganism strain or target cellular analyte is bound to the laminated article; and d) detecting the presence of the at least one bound microorganism strain or bound target cellular analyte.

Embodiment 46 is a method of detecting microorganisms or target cellular analytes in a fluid sample. The method includes a) providing a plurality of guanidine-functionalized perlite particles according to any one of embodiments 25 to 31; b) providing a fluid sample suspected of containing at least one microorganism strain or target cellular analyte; c) contacting the fluid sample with the plurality of guanidine-functionalized perlite particles such that at least a portion of the at least one microorganism strain or target cellular analyte is bound to the guanidine-functionalized perlite particles; and d) detecting the presence of the at least one bound microorganism strain or bound target cellular analyte.

Embodiment 47 is the method of embodiment 45 or embodiment 46, wherein the detecting includes a culture-based method, an imaging method, an immunological detection method, a genetic detection method, a bioluminescence method, or a combination thereof.

Embodiment 48 is the method of any of embodiments 45 to 47, wherein the detecting includes a bioluminescence method.

Embodiment 49 is the method of any of embodiments 45 to 48, further including contacting the at least one bound microorganism strain with a lysis agent.

Embodiment 50 is the method of any of embodiments 45 to 49, wherein the bound target cellular analyte includes a nucleic acid, a protein, a cell wall component, ATP, or a combination thereof.

Embodiment 51 is the method of any of embodiments 45 to 50, wherein the bound target cellular analyte includes ATP.

Embodiment 52 is the method of embodiment 45, wherein the contacting includes passing the fluid sample at least once through the laminated article.

Embodiment 53 is the method of embodiment 45 or embodiment 52, wherein the contacting includes passing the fluid sample through the laminated article at a pressure of 4.0 pounds per square inch (psi) (27.58 kilopascals (kPa)) or less.

Embodiment 54 is the method of embodiment 45 or embodiment 52, wherein the contacting includes passing the fluid sample through the laminated article at a pressure of 0.5 psi (3.4 kPa) or less.

Embodiment 55 is the method of any of embodiments 45 to 54, wherein the microorganism strain is selected from strains of bacteria, fungi, protozoans, viruses, bacterial endospores, and combinations thereof.

Embodiment 56 is the nonwoven article of any of embodiments 1 to 24, wherein the nonwoven article has a basis weight in the range of about 150 to about 350 grams per square meter ($g/m^2$).

EXAMPLES

Unless otherwise noted, all chemicals used in the examples can be obtained from Sigma-Aldrich Corp. (Saint Louis, Mo.). Unless otherwise specified, all microbiological supplies and reagents were purchased as standard products from either Sigma-Aldrich or VWR.

| Material | Vendor |
| --- | --- |
| Fiber 1 - SHORT STUFF E380F ~0.7 mm average length, 15 microns diameter polyethylene fibers | MiniFIBERS, Inc.; Johnson City, TN |
| Fiber 2 - 6 denier 2 inches long chopped nylon fibers | MiniFIBERS, Inc.; Johnson City, TN |
| Fiber 3 - 1 denier bi-component ethylene vinyl acetate/polypropylene fibers | MiniFIBERS, Inc.; Johnson City, TN |
| Fiber 4 - long glass fibers (MICRO-STRAND 106-475 Glass Fiberglas) Schuller Inc. | Johns Mansville; Denver, CO |
| Perlite 4106 - perlite powder | Dicaperl Minerals Corporation, Crawfordsville, IN |
| Perlite 4156 - perlite powder | Dicaperl Minerals Corporation, Crawfordsville, IN |
| Perlite 476 - perlite powder | Dicaperl Minerals Corporation, Crawfordsville, IN |
| DE - diatomaceous earth particles | Dicaperl Minerals Corporation, Crawfordsville, IN |
| *Escherichia coli* ATCC 11229 | American Type Culture Collection, Manassas, VA |
| *Staphylococcus aureus* ATCC 6538 | American Type Culture Collection, Manassas, VA |
| DI Water - Deionized filtered 18 megaohm water from a Milli-Q Gradient System | Millipore; Waltham, MA |
| ATP free water - HYPURE Molecular biology grade water, Catalog #SH30538.02 | Thermo Fisher Scientific; Waltham, MA |
| CLEAN-TRACE pure ATP standard - reagent for bioluminescence assay | 3M Company; Bridgend, UK |
| CLEAN-TRACE lysis reagent - reagent for bioluminescence assay | 3M Company; Bridgend, UK |
| CLEAN-TRACE luciferin-luciferase enzyme reagent - reagent for bioluminescence assay | 3M Company; Bridgend, UK |
| Tryptic Soy Broth - DIFCO Tryptic Soy Broth, prepared at 3% according to the manufacturer's instructions | Becton Dickenson; Sparks MD |
| TSA plate - plates prepared according to manufacturer's instructions with 3 wt % Tryptic Soy Agar powder | Becton Dickenson; Sparks MD |
| PAC - 3M PETRIFILM Aerobic Count Plates | 3M Company; St. Paul MN |
| BBL Buffer - Butterfield's buffer, pH 7.2 ± 0.2, monobasic potassium phosphate buffer solution (VWR Catalog Number 83008-093) | VWR; West Chester, PA |
| 3M CLEAN-TRACE NG luminometer | 3M Company, Bridgend, UK |
| Cuvettes - Greiner Bio-One polystyrene 4 mL tubes | VWR; West Chester, PA |
| Microfuge tubes - 1.5 mL BrandTech polypropylene tubes | VWR; West Chester, PA |
| 0.22 micron filter - Whatman Catalog # 111106 | GE Healthcare Life Sciences; Pittsburgh, PA |

Preparation of Guanylated Perlite Particles

Example 1

A solution of 3-aminopropyltrimethoxysilane (17.9 g, 100 mmol) dissolved in anhydrous methanol (85 mL) was treated with of O-methylisourea hemisulfate (12.3 g, 50 mmol). The reaction mixture was stirred under an atmosphere of nitrogen overnight. A portion of this solution (50 g) was transferred to a 500 mL round bottom flask and diluted with 200 mL of anhydrous methanol. Perlite 4106 particles (50 g) were then added to the flask followed by the addition of DI water (0.9 mL, 50 mmol). The mixture was stirred rapidly for three days to facilitate reaction between the trimethoxysilane and the particles. The resulting guanidine-functionalized perlite particles were isolated by filtration, rinsed with methanol, followed by water, and allowed to air dry. The particles were then dried in a vacuum oven at 70° C. overnight. The percent nitrogen content as measured by ECSA is shown in Table 1 below.

TABLE 1

Surface composition of guanidine-functionalized perlite particles by XPS

| Sample | Rep | C | N | O | F | Na | Al | Si | S | K | Ca | Fe | Ag | avg. % N | stdev. % N |
| --- | --- | --- | --- | --- | --- | --- | --- | --- | --- | --- | --- | --- | --- | --- | --- |
| perlite | A | 5.8 | 0.0 | 64 | 0.2 | 2.1 | 3.5 | 22 | 0.0 | 1.9 | 0.1 | 0.03 | 0.00 | 0.1 | 0.10 |
| perlite | B | 5.8 | 0.2 | 64 | 0.2 | 1.9 | 3.6 | 22 | 0.0 | 2.3 | 0.1 | 0.10 | 0.00 | | |
| perlite | C | 5.3 | 0.1 | 64 | 0.2 | 2.2 | 3.5 | 22 | 0.0 | 2.3 | 0.1 | 0.06 | 0.00 | | |
| g-perlite | A | 11 | 6.2 | 57 | 0.2 | 1.1 | 2.8 | 20 | 0.5 | 1.0 | 0.1 | 0.03 | 0.00 | 5.9 | 0.35 |
| g-perlite | B | 11 | 5.8 | 57 | 0.5 | 1.3 | 2.9 | 20 | 0.4 | 0.9 | 0.1 | 0.07 | 0.00 | | |
| g-perlite | C | 10 | 5.5 | 58 | 0.6 | 1.1 | 2.9 | 20 | 0.5 | 1.0 | 0.1 | 0.02 | 0.01 | | |

Testing of Guanylated Perlite for ATP Capture

Example 2

12 mg each of guanidine-functionalized perlite powder (of Example 1) and untreated perlite (Comparative Example 1, CE 1) were aliquoted in cuvettes. A stock of ATP spiked water sample containing the ATP standard was prepared such that each milliliter of sample would contain 3000 RLUs ATP signal (about 7 microliters of ATP standard per milliliter of water). To the cuvette tubes, 1 milliliter of spiked sample was added, the tubes were capped, and the tubes were set on a rotating platform (Thermolyne VARI MIX rocking platform (Barnstead International, Iowa) at 14 cycles/minute for 10 minutes. Next, the tubes were put in test tube stands to settle the powder for 10 minutes. Supernatant samples were removed into another cuvette, of which 100 microliters were removed and tested for ATP assay.

A volume of 300 microliters of luciferase enzyme was added to the cuvette containing the settled powder. The contents were mixed by vortexing for 5 seconds, then the cuvette was connected to the adaptor (custom made 12 centimeters (cm) long, 1 cm in diameter made from DELRIN material) and read in the NG luminometer. Similarly, a volume of 300 microliters of luciferase enzyme was added to the cuvette and mixed on a vortex mixer for 10 seconds. The cuvette was connected to an adaptor and read in the NG luminometer. Supernatants were analyzed for mass balance purposes. A 100 microliter volume from the spiked stock was tested for ATP signal, which was multiplied by 10 to account for the 1 milliliter test sample. The average total ATP signal in RLUS per 1 ml sample was 318.75×10=3187.5 RLUs=3188 RLUs. % ATP Capture=(RLUs from settled powder/RLUs from 1 ml spiked sample)×100
The results are reported in Table 2 below.

TABLE 2

| Sample | Ave ATP signal (in RLUs) | % ATP Capture |
|---|---|---|
| 1 ml ATP spiked sample | 3188 | N/A |
| Example 2 - powder | 2278 | 71.45% |
| Example 2 - supernatant | 307 | 9.61% |
| CE 1 - powder | 22 | 0.69% |
| CE 1 - supernatant | 2277 | 71.41% |

N = 3, standard deviation <10% unless noted

The same testing was set up with perlite powders with 1 ml water (no ATP) as a background control. The background ATP signal for the guanidine-functionalized powder of Example 1 was 2.3 RLUS, whereas for the perlite powder of CE 1 it was 3.6 RLUS.

Preparation of Fibrous Porous Matrices Containing Guanylated Perlite

Examples 3 and 4

Two fiber premixes were prepared by mixing various amounts of Fiber 1, Fiber 2, Fiber 3, and Fiber 4 as shown in Table 3 below. The fibers were added to 3 liters of cold deionized water in a 4 L blender (available from VWR, Radnor, Pa., under the trade designation "WARING COMMERCIAL HEAVY DUTY BLENDER, MODEL 37BL84") and blended at low speed for 30 seconds. The mixture was examined for uniform dispersion of the fibers without nits or clumps. The guanidine-functionalized perlite particles from Example 1 were added with an additional liter of deionized water and mixed at low speed for 15 seconds.

A nonwoven fibrous porous felt was prepared using a pad maker apparatus (obtained from Williams Apparatus, Watertown, N.Y., under the trade designation "TAPPI") that had a box measuring about 30 centimeters (12 inches) square and 30 centimeters (12 inches) high with a fine mesh screen at the bottom and a drain valve. On the screen ~ a 14 inch×12 inch piece of a polyethylene spunbond (PET Lutradur 7240 obtained from Fiberweb, Cincinnati, Ohio) was laid as scrim on the screen. The box was filled with tap water up to a height of about 1 centimeter above the screen. Each fiber and additive mixture was poured into the box and the valve was opened immediately which created a vacuum that pulled the water out of the box.

The fibrous porous felt was transferred from the apparatus onto a 20 centimeter square sheet of blotter paper (96-pound white paper, obtained from Anchor Paper, St. Paul, Minn.). The fibrous porous felt was sandwiched between 2 to 4 layers of blotter paper, to blot excess water. The pressed fibrous porous felt was then transferred onto a fresh sheet of blotter paper and placed in an oven (obtained from SPX Thermal Product Solutions, White Deer, Pa., under the trade designation "BLUE M STABIL-THERM OVEN, MODEL OV-560A2") set at 110° C. for about 3 hours to remove residual water and to form a nonwoven fibrous porous matrix. The resulting fibrous porous matrix of Example 3 was approximately 0.8-1 millimeter thick, while the fibrous porous matrix of Example 4 was 0.5-0.8 mm thick.

TABLE 3

| Material (grams) | Example 3 | Example 4 |
|---|---|---|
| Fiber 1 | 11.16 | 8.87 |
| Fiber 2 | 3.04 | 2.47 |
| Fiber 3 | 2.33 | 1.85 |
| Fiber 4 | 1.77 | 1.45 |
| g-perlite | 5.01 | 4.02 |
| Basis weight (g/m$^2$) | 244.89 | 195.55 |

Testing of Fibrous Porous Matrix with Guanylated Perlite for *E. coli* and *S. aureus* Bacterial Capture and ATP Detection A single colony from a streak culture of *E. coli* (ATCC 51813, a Gram negative organism) was inoculated into 10 ml of TSB (Tryptic Soy Broth, 3% by weight from Difco) and incubated overnight for about 20 hours at 37° C. The resulting bacterial stock contained about 1×10$^9$ cfus/ml. That stock was serially diluted in DI water to make a working stock of 1×10$^5$ cfus/ml.

14 mm disks of the fibrous porous matrix of Example 3 were die punched and inserted into 13 mm filter holders (SWINNEX holders obtained from Millipore). One ml of the above working stock of *E. coli* was filtered through each disk using a 1 cc syringe. The filtrate was discarded. Each disk was removed from the holder and placed in a cuvette. A volume of 100 microliters of the lysis reagent was added to the disk and vortexed for 10 seconds. A volume of 300 microliters of luciferase enzyme was added to the cuvette and vortexed for 10 seconds. The cuvette was connected to the adaptor (custom made in 3M machine shop, 12 cm long, 1 cm in diameter, made from DELRIN material) and read in the NG luminometer. Disks through which 1 ml of unspiked DI water was filtered were also tested, for background ATP signal. Another set of disks was prepared, to which a 100 microliter volume from a 1×10$^5$ cfus/ml dilution was spiked. This spiked disk was tested for ATP signal (in RLUs) and was the "100% control" sample. 14 mm disks from the fibrous porous matrix of Example 4 were also tested as described for the matrices of Example 3. Capture efficiency was calculated using the formula below. The results are shown in Table 4.

% Capture Efficiency=(RLUs from test fibrous porous matrix disk/RLUs from the 100% Control)×100

TABLE 4

| Example | Sample | ATP signal (in RLUs) | % Capture Efficiency |
|---|---|---|---|
| N/A | 100% Control for Matrix of Example 3 | 1653 (39%) | N/A |
| Example 5 | Matrix of Example 3 | 1105 | 67 (40%) |
| N/A | 100% Control for Matrix of Example 4 | 1932 (3%) | N/A |
| Example 6 | Matrix of Example 4 | 1632 | 85 | n = 2, % standard deviation indicated in parentheses if greater than 10%. The background ATP signal for the matrices of Examples 3 and 4 was 348 RLUs and 175 RLUs, respectively, and was subtracted from the signal of the spiked disks.

Capture and detection of *S. aureus* (ATCC 6538, a Gram positive organism) using the fibrous porous matrices of Examples 3 and 4 were performed according to the method described above for *E. coli*. The results are shown in Table 5 below.

TABLE 5

| Matrix | Sample | ATP signal (in RLUs) | % Capture Efficiency |
|---|---|---|---|
| N/A | 100% Control for Example 7 | 1785 (35%) | N/A |
| Example 3 | Example 7 | 987 | 55 (21%) |
| N/A | 100% Control for Example 8 | 1260 (23%) | N/A |
| Example 4 | Example 8 | 768 | 61 (21%) | n = 2, % standard deviation indicated in parentheses if greater than 10%. The background ATP signal for Examples 7 and 8 were 348 RLUS and 175 RLUS, respectively, and were subtracted from the signal of the spiked matrices.

Preparation of Guanylated Diatomaceous Earth

Comparative Example 3

50 g of diatomaceous earth particles were guanylated according to the method described above according to Example 1, except that a 48 g portion of the reaction mixture solution was transferred to a 500 ml round bottom flask and diluted with 200 ml of anhydrous methanol (instead of a 50 g portion). The particles were dried in a vacuum oven at 70° C. overnight to give 47 g of guanidine-functionalized diatomaceous earth. The % nitrogen content as measured by ECSA is shown in Table 6 below.

Testing of Guanylated DE for ATP Capture 12 mg each of guanidine-functionalized diatomaceous earth (DE) powder of Comparative Example 3 (CE 3) and untreated DE powder (Comparative Example 4, CE 4) were aliquoted in cuvettes. A stock of ATP spiked water sample containing ATP standard was prepared such that each ml of sample would contain 3000 RLUs ATP signal (32 microliters of ATP standard per ml water). The test was performed as described in Example 2 above. The average total ATP signal in RLUS per 1 ml sample was 240×10=2400 RLUs. % ATP Control=(RLUs from settled powder/RLUs from 1 ml spiked sample)×100. The results are shown in Table 7 below.

TABLE 7

| Sample | Ave ATP signal (in RLUs) | % ATP Control |
|---|---|---|
| 1 ml ATP spiked sample | 2400 | 100% |
| CE 3 - powder | 151 | 6.29 |
| CE 3 - supernatant | 385 | 16 (12%) |
| CE 4 - powder | 4.25 | 0.18 |
| CE 4 - supernatant | 1500 | 63 (12%) |

N = 2, standard deviation <10% unless noted in parentheses

The same testing was set up with DE powders, with 1 ml water (containing no ATP) as a background control. The background ATP signal for the guanidine-functionalized DE powder of CE 3 was 6 RLUs, whereas for the DE powder of CE 4 it was 4.5 RLUs.

Preparation of Guanylated Perlite 476 and 4156

Examples 9 and 10

Perlite 476 particles and perlite 4156 particles (50 g each) were guanylated as described above in Example 1, except that 48 g of the reaction mixture solution was transferred to a 500 ml round bottom flask and diluted with 200 ml of anhydrous methanol (instead of a 50 g portion). The particles were then dried in a vacuum over at 60° C. overnight to give 49 g each of guanidine-functionalized perlite 476 particles (Example 9) and guanidine-functionalized perlite 4156 particles (Example 10. The % nitrogen content as measured by ECSA is shown in Table 8 below.

TABLE 6

XPS Surface Concentrations (Atomic %)

| Sample | Rep | C | N | O | F | Na | Al | Si | S | K | Ca | Fe | Ag | avg. % N | stdev. % N |
|---|---|---|---|---|---|---|---|---|---|---|---|---|---|---|---|
| perlite | A | 5.8 | 0.0 | 64 | 0.2 | 2.1 | 3.5 | 22 | 0.0 | 1.9 | 0.1 | 0.03 | 0.00 | 0.1 | 0.10 |
| perlite | B | 5.8 | 0.2 | 64 | 0.2 | 1.9 | 3.6 | 22 | 0.0 | 2.3 | 0.1 | 0.10 | 0.00 | | |
| perlite | C | 5.3 | 0.1 | 64 | 0.2 | 2.2 | 3.5 | 22 | 0.0 | 2.3 | 0.1 | 0.06 | 0.00 | | |
| g-perlite | A | 11 | 6.2 | 57 | 0.2 | 1.1 | 2.8 | 20 | 0.5 | 1.0 | 0.1 | 0.03 | 0.00 | 5.9 | 0.35 |
| g-perlite | B | 11 | 5.8 | 57 | 0.5 | 1.3 | 2.9 | 20 | 0.4 | 0.9 | 0.1 | 0.07 | 0.00 | | |
| g-perlite | C | 10 | 5.5 | 58 | 0.6 | 1.1 | 2.9 | 20 | 0.5 | 1.0 | 0.1 | 0.02 | 0.01 | | |
| diatom. earth | A | 4.9 | 0.1 | 65 | 1.2 | 1.9 | 3.2 | 22 | 0.0 | 1.5 | 0.1 | 0.09 | 0.00 | 0.2 | 0.11 |
| diatom. earth | B | 4.9 | 0.2 | 65 | 1.2 | 1.9 | 3.2 | 22 | 0.0 | 1.6 | 0.1 | 0.11 | 0.00 | | |
| diatom. earth | C | 4.1 | 0.3 | 65 | 1.1 | 2.0 | 3.2 | 23 | 0.0 | 1.7 | 0.1 | 0.09 | 0.00 | | |
| g-d.e. | A | 10 | 5.7 | 57 | 0.4 | 1.3 | 2.8 | 21 | 0.7 | 1.1 | 0.0 | 0.10 | 0.03 | 5.4 | 0.24 |
| g-d.e. | B | 9.5 | 5.2 | 58 | 0.4 | 1.2 | 2.9 | 21 | 0.6 | 1.1 | 0.1 | 0.09 | 0.01 | | |
| g-d.e. | C | 9.5 | 5.4 | 58 | 0.4 | 1.1 | 2.7 | 21 | 0.6 | 1.1 | 0.1 | 0.11 | 0.02 | | |

TABLE 8

| | | XPS Surface Concentrations (Atomic %) | | | | | | | | | | |
|---|---|---|---|---|---|---|---|---|---|---|---|---|
| Sample | Area | C | N | O | F | Na | Al | Si | S | K | Ca | Fe |
| perlite 476 control | A | 7.2 | 0.0 | 62 | 0.0 | 2.1 | 3.5 | 23 | 0.0 | 2.1 | 0.1 | 0.05 |
| perlite 476 control | B | 7.3 | 0.0 | 62 | 0.1 | 1.8 | 3.3 | 23 | 0.0 | 2.0 | 0.1 | 0.11 |
| perlite 476 control | C | 6.9 | 0.0 | 62 | 0.0 | 2.1 | 3.5 | 23 | 0.0 | 2.4 | 0.1 | 0.11 |
| g-perlite 476 | A | 12 | 5.6 | 55 | 0.3 | 1.3 | 3.0 | 21 | 0.5 | 1.2 | 0.1 | 0.14 |
| g-perlite 476 | B | 12 | 5.6 | 55 | 0.3 | 1.2 | 2.9 | 21 | 0.5 | 1.0 | 0.1 | 0.04 |
| g-perlite 476 | C | 11 | 5.2 | 56 | 0.4 | 1.2 | 3.2 | 21 | 0.4 | 1.3 | 0.1 | 0.21 |
| perlite 4156 control | A | 6.7 | 0.1 | 62 | 0.3 | 2.1 | 3.6 | 23 | 0.0 | 2.2 | 0.1 | 0.01 |
| perlite 4156 control | B | 6.4 | 0.1 | 62 | 0.3 | 2.1 | 3.7 | 23 | 0.0 | 2.3 | 0.1 | 0.00 |
| perlite 4156 control | C | 6.0 | 0.1 | 62 | 0.3 | 1.9 | 3.6 | 23 | 0.0 | 2.5 | 0.1 | 0.16 |
| g-perlite 4156 | A | 10 | 4.2 | 57 | 0.4 | 1.3 | 3.3 | 22 | 0.3 | 1.3 | 0.1 | 0.09 |
| g-perlite 4156 | B | 10 | 4.6 | 57 | 0.4 | 1.1 | 3.3 | 22 | 0.4 | 1.3 | 0.1 | 0.21 |
| g-perlite 4156 | C | 10 | 4.4 | 57 | 0.3 | 1.4 | 3.2 | 22 | 0.4 | 1.4 | 0.1 | 0.10 |

Testing of Guanylated Perlite 476 and Perlite 4156 for ATP Capture

Examples 11 and 12

12 mg each of the powder of guanidine-functionalized perlite 476 (Example 11), untreated Perlite 476 (Comparative Example 5, CE 5), guanidine-functionalized perlite 4156 (Example 12), and untreated Perlite 4156 (Comparative Example 6, CE 6) were aliquoted in cuvettes. A stock of ATP spiked water sample containing the ATP standard was prepared such that each ml of sample would contain 3000 RLUs ATP signal (32 microliters of ATP standard per ml water). The test was performed as described in Example 2 above. The average total ATP signal in RLUs per 1 ml sample was 240×10=2400 RLUs. % ATP Control=(RLUs from settled powder/RLUs from 1 ml spiked sample)×100. The results are shown in Table 9 below.

TABLE 9

| Sample | Ave ATP signal (in RLUs) | % ATP Control |
|---|---|---|
| 1 ml ATP spiked sample | 2400 | 100 |
| perlite 476 powder (CE 5) | 10 | 0.6 (81%) |
| perlite 476 supernatant (CE 5 supernatant) | 1510 | 63 |
| g-perlite 476 powder | 1596 | 67 |
| g-perlite 476 supernatant | 165 | 7 (56%) |
| perlite 4156 powder (CE 6) | 10 | 0.6 (82%) |
| perlite 4156 supernatant (CE 6 supernatant) | 2025 | 84 |
| g-perlite 4156 powder | 1602 | 68 |
| g-perlite 4156 supernatant | 110 | 5 |

N = 2, standard deviation <10% unless noted in parentheses

The same testing was set up with powders with 1 ml water (containing no ATP) as a background control. The background ATP signal for guanidine-functionalized perlite 476 powder was 40 RLUs, CE 5 was 7 RLUs, guanidine-functionalized perlite 4156 powder was 41 RLUs, and CE 6 was 4 RLUs. The background signals for guanidine-functionalized perlite 476 and 4156 were subtracted from the ATP capture signal.

Testing of Example 3 for Rapid Microbial Monitoring in Produced Water Samples

Produced water samples were obtained from an oil well in Canada. Samples were serially diluted in BBL buffer and plated 1 ml each on PAC plates. The plates were incubated at 37° C. for 48 hours, per manufacturer instructions. The plates were analyzed for bacterial counts using the 3M PETRIFILM Plate Reader. A one hundred microliter volume from each sample was added to a cuvette and mixed with 145 microliters of the CLEAN-TRACE Water-Plus Total ATP extractant and vortexed for 10 seconds. A volume of 450 microliters of the CLEAN-TRACE Water-Plus Total ATP enzyme was added, then mixed for 10 seconds. Using an adaptor (described above with respect to Examples 5 and 6) the cuvette was inserted into the NG luminometer to measure the ATP signal.

Based on the volumes filtered, colony counts and ATP values, two samples were further selected for microbial testing with the nonwoven fibrous porous matrices of Example 3. Sample E (Comparative Example 8, CE 8) had approximately $3 \times 10^2$ cfus/ml, a free (non-microbial) ATP signal of 25 RLUs, and a total ATP signal of 46 RLUs. Sample G (Comparative Example 9, CE 9) had $4.7 \times 10^5$ cfus/ml, a free (non-microbial) ATP signal of 39 RLUs, and a total ATP signal of 315 RLUs.

A 10 ml volume from each produced water sample was processed through 14 mm disks of the fibrous porous matrix of Example 3 and 0.22 micron filter (Comparative Example 7, CE 7) to evaluate filtration capability. Filtration was terminated once flow through stopped due to clogging. The volumes prior to clogging are shown in Table 10 below.

TABLE 10

| Produced Water sample # | Volume through CE 7 (in ml) | Volume through Example 3 (in ml) |
|---|---|---|
| Sample A | 10 | 10 |
| Sample B | 2 | 10 |
| Sample C | 0.5 | 10 |
| Sample D | 4.5 | 10 |
| Sample E | 0.5 | 10 |
| Sample F | 1 | 10 |
| Sample G | 10 | 10 |
| Sample H | 10 | 10 |

14 mm disks of the nonwoven fibrous porous matrix of Example 3 were die punched and inserted into 13 mm filter holders (SWINNEX holders obtained from Millipore). Ten ml of produced water sample E was filtered through a disk using a 10 cc syringe. The filtrate was discarded. The disk was removed from the holder and tested for the ATP signal as described above for produced water samples. A second disk was processed the same, except that it was washed with 10 ml DI water prior to analysis for the ATP signal.

Fibrous porous matrix disks through which 10 ml of unspiked DI water was filtered were tested for background ATP signal. The background signal was 253 RLUs and was subtracted from test readings. The improvement in ATP signal from captured bacteria over a CLEAN-TRACE test (without concentrating the bacteria in a nonwoven fibrous porous matrix) was calculated using the formula below. The results are shown in Table 11 below.

The fold increase in ATP signal over a CLEAN-TRACE test (without concentrating the bacteria in a nonwoven fibrous porous matrix)=(RLUs from post filtration wet-laid disk/RLUs from 100 microliters of unfiltered sample).

Free (non-microbial) ATP content in CE 8 and in disks of the matrix of Example 3 (washed and not washed) was analyzed by using 450 microliters of the CLEAN-TRACE Water-Plus Total ATP enzyme, mixing for 10 seconds, and reading the ATP signal in the NG luminometer.

TABLE 11

| Matrix | Produced Water sample | Ave Free ATP signal (in RLUs) | Ave Total ATP signal (in RLUs) | Fold increase over current test in Total ATP |
|---|---|---|---|---|
| Example 3 (not washed) | E | 27 (93) | 3408 (52) | 61 |
| Example 3 (washed) | E | 6507 (86) | 71613 | 1279 |
| CE 8 | E | 25 (73) | 56 (35) | N/A |
| Example 3 (not washed) | G | 883 | 11653 | 37 |
| Example 3 (washed) | G | 624 (22) | 23578 | 72 |
| CE 9 | G | 39 (13) | 315 | N/A |

N = 2, standard deviation less than 10% unless otherwise noted in parentheses

Comparative Examples 8 and 9 were evaluated for turbidity using a Micro 100 Turbidimeter. DI water was used a reference standard. CE 8 had an average turbidity of 138 NTUs and CE 9 had an average turbidity of 0.96, while DI water had a turbidity of 0.02 NTUs. Example CE 8 had to be diluted 4 fold in DI water in order to get the measurements. Thus, the reported turbidity for CE 8 is 4 times the actual measurement (4×34.5).

The variation in tests suggests matrix interference. The improvement in ATP signal after washing indicates the decrease in carryover of inhibitory substances, which allows the ATP assay to be used for rapid monitoring of produced water samples following washing.

Guanylated Perlite Immobilized within Spunbond Scrims (Prophetic Example)

A spunbond substrate with an average pore size less than the average pore size of the guanidine-functionalized particles of Example 1 is laid flat on a clean bench. A 16 mm diameter circular area is marked on the substrate. A 15 mg aliquot of the material of Example 1 is weighed out and placed on the marked area. This is repeated three times to make three replicate samples. Another sheet of a spunbond substrate is laid flat on top of the areas with the weighed powder. The top sheet is carefully flattened. The marked area is ultrasonically welded using a BRANSON 2000d ULTRASONIC WELDER. The ultrasonic horn has an outer diameter of 18 mm and an inner diameter of 16 mm. The welding is performed on a flat aluminum plate at a setting of 250 Joules.

The welded laminated articles are cut off using scissors and placed into Swinnex holders for ATP capture studies as described above in Example 2. Briefly, one milliliter of DI water is spiked with 3000 RLUs ATP and is filtered through the laminated article using a 1 cc syringe. After filtration the laminated article is removed from the filter holder and added to a cuvette. 145 microliters of the CLEAN-TRACE Water-Plus Total ATP extractant is added to the cuvette. The cuvette is vortexed for 10 seconds. A volume of 450 microliters of the CLEAN-TRACE Water-Plus Total ATP enzyme is added, then mixed for 10 seconds. The cuvette is connected to the adaptor (as described in Example 2 above) and is read in the NG luminometer.

Laminated articles are also tested for background signal by filtering one ml of unspiked deionized water through them. The background signal is subtracted from the test signal. A one hundred microliter aliquot of the stock ATP solution is tested to generate a signal that is multiplied by 10 to generate a "100% Control" signal. % ATP Control=(RLUs from laminated article/RLUs from 1 ml spiked sample)× 100.

While the specification has described in detail certain exemplary embodiments, it will be appreciated that those skilled in the art, upon attaining an understanding of the foregoing, may readily conceive of alterations to, variations of, and equivalents to these embodiments. Furthermore, all publications and patents referenced herein are incorporated by reference in their entirety to the same extent as if each individual publication or patent was specifically and individually indicated to be incorporated by reference. Various exemplary embodiments have been described. These and other embodiments are within the scope of the following claims.

What is claimed is:

1. A guanidine-functionalized perlite particle comprising a perlite particle that is modified with at least one silane having the formula $$X_{3-n}R^a{}_n Si\text{—}Y\text{-}G,$$

wherein:
n is 0, 1, or 2;
each $R^a$, if present, is independently an alkyl, aralkyl, or aryl;
Y is a divalent group comprising an alkylene having 2 to 20 carbons;
G is a guanidine group of the formula —NH—C(=NH)—NH$_2$; and
each X is independently alkoxy or acyloxy.

2. The guanidine-functionalized perlite particle of claim 1, wherein the divalent group further comprises an arylene, oxy, —NH—, or a combination thereof.

3. The guanidine-functionalized perlite particle of claim 1, wherein the divalent group is alkylene having 3 to 6 carbons.

4. The guanidine-functionalized perlite particle of claim 1, wherein the guanidine group is the reaction product of a primary amine and an O-methylisourea salt.

5. The guanidine-functionalized perlite particle of claim 4, wherein the primary amine is 3-aminopropyltrimethoxysilane.

6. The guanidine-functionalized perlite particle of claim 1, having a surface nitrogen content of at least 2 atomic percent as measured by x-ray photoelectron spectroscopy (XPS).

7. A nonwoven article comprising a) a fibrous porous matrix and b) a plurality of guanidine-functionalized perlite particles enmeshed in the fibrous porous matrix, and wherein each of the guanidine-functionalized perlite particles comprises a perlite particle that is modified with at least one silane having the formula $$X_{3-n}R^a{}_n Si\text{—}Y\text{-}G,$$

wherein:
n is 0, 1, or 2;
each $R^a$, if present, is independently an alkyl, aralkyl, or aryl;
Y is a divalent group comprising an alkylene having 2 to 20 carbons;
G is a guanidine group of the formula —NH—C(=NH)—NH$_2$; and
each X is independently alkoxy or acyloxy.

8. The nonwoven article of claim 7, wherein the fibrous porous matrix has a thickness of between 0.15 millimeters and 2 millimeters.

9. The nonwoven article of claim 7, wherein the fibrous porous matrix is a nonwoven fibrous layer comprising polymeric fibers and inorganic fibers.

10. The nonwoven article of claim 7, wherein the fibrous porous matrix is a nonwoven fibrous layer and the guanidine-functionalized perlite particles are distributed throughout the nonwoven fibrous layer.

11. The nonwoven article of claim 7, wherein the fibrous porous matrix is a nonwoven fibrous layer comprising uncrimped polymeric fibers.

12. A laminated article comprising:
a. a first substrate;
b. a second substrate sealed to the first substrate along at least a portion of a perimeter of the first substrate; and
c. a plurality of guanidine-functionalized perlite particles disposed between the first substrate and the second substrate, wherein each of the guanidine-functionalized perlite particles comprises a perlite particle that is modified with at least one silane having the formula

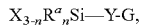
$X_{3-n}R^a_n\text{Si}$—Y-G, wherein:
n is 0, 1, or 2;
each $R^a$, if present, is independently an alkyl, aralkyl, or aryl;
Y is a divalent group comprising an alkylene having 2 to 20 carbons;
G is a guanidine group of the formula —NH—C(=NH)—NH$_2$; and
each X is independently alkoxy or acyloxy.

13. The laminated article of claim 12, wherein the first substrate and the second substrate are independently selected from a spunbond polypropylene, a spunbond polyamide, a spunbond blend of polyamide and polyester, a spunbond polyethylene, a spunbond polyester, a spunbond polybutylene terephthalate, and a spunbond polypropylene.

14. A method of detecting microorganisms or target cellular analytes in a fluid sample, the method comprising:
a) providing a laminated article according to claim 12;
b) providing a fluid sample suspected of containing at least one microorganism strain or target cellular analyte;
c) contacting the fluid sample with the laminated article such that at least a portion of the at least one microorganism strain or target cellular analyte is bound to the laminated article; and
d) detecting the presence of the at least one bound microorganism strain or bound target cellular analyte.

15. The method of claim 14, wherein the detecting comprises a bioluminescence method.

16. The method of claim 14, wherein the bound target cellular analyte comprises a nucleic acid, a protein, a cell wall component, ATP, or a combination thereof.

17. The method of claim 14, wherein the contacting comprises passing the fluid sample through the laminated article at a pressure of 4.0 pounds per square inch (psi) (27.58 kilopascals (kPa)) or less.

18. A method of detecting microorganisms or target cellular analytes in a fluid sample, the method comprising:
a) providing a plurality of guanidine-functionalized perlite particles according to claim 1;
b) providing a fluid sample suspected of containing at least one microorganism strain or target cellular analyte;
c) contacting the fluid sample with the plurality of guanidine-functionalized perlite particles such that at least a portion of the at least one microorganism strain or target cellular analyte is bound to the guanidine-functionalized perlite particles; and
d) detecting the presence of the at least one bound microorganism strain or bound target cellular analyte.

* * * * *

UNITED STATES PATENT AND TRADEMARK OFFICE
CERTIFICATE OF CORRECTION

PATENT NO.        : 10,427,131 B2
APPLICATION NO.   : 15/555679
DATED             : October 1, 2019
INVENTOR(S)       : Manjiri Kshirsagar It is certified that error appears in the above-identified patent and that said Letters Patent is hereby corrected as shown below:

In the Specification

Column 2,
Line 1, delete "(triethoxysilyI)" and insert -- (triethoxysilyl) --, therefor.
Line 5, delete "(2-Arninoethyl)" and insert -- (2-Aminoethyl) --, therefor.

Column 3,
Lines 18-20, delete "The term "and/or" means either or both. For example "A and/or B" means only A, only B, or both A and B." and insert the same on Column 3, Line 19 as a new paragraph.

Column 12,
Line 9, delete "[(amino(polypropylenoxy)]" and insert -- [(amino(polypropylenoxy))] --, therefor.

Column 24,
Line 26, delete "anthracia," and insert -- anthracis, --, therefor.

Column 26,
Line 15, delete "enolysins." and insert -- endolysins. --, therefor.
Line 50, delete "adensosine" and insert -- adenosine --, therefor.

Column 33,
Line 9, delete "3000" and insert -- ~3000 --, therefor.
Line 33, after "100" insert -- . --.

Column 36,
Line 8, delete "3000" and insert -- ~3000 --, therefor.

Column 37,
Line 29, delete "3000" and insert -- ~3000 --, therefor.

Signed and Sealed this
Nineteenth Day of November, 2019

Andrei Iancu
*Director of the United States Patent and Trademark Office*

Column 39,
Line 63, delete "3000" and insert -- ~3000 --, therefor.